US012653694B2

(12) United States Patent
Smith et al.

(10) Patent No.: US 12,653,694 B2
(45) Date of Patent: Jun. 16, 2026

(54) EXPANDABLE INTERBODY FUSION DEVICE FOR USE WITH POSTERIOR TO LATERAL APPROACH

(71) Applicant: Jeffrey Scott Smith, Granbury, TX (US)

(72) Inventors: Noah M. Smith, Ft. Worth, TX (US); Jeffrey Scott Smith, Granbury, TX (US); Braden R. Trejo, Austin, TX (US); Zachary M. Keeney, Seattle, WA (US); Joseph T. LeCheminant, Palmer, AK (US)

(73) Assignee: Jeffrey Smith, Granbury, TX (US)

( * ) Notice: Subject to any disclaimer, the term of this patent is extended or adjusted under 35 U.S.C. 154(b) by 1113 days.

(21) Appl. No.: 17/686,060

(22) Filed: Mar. 3, 2022

(65) Prior Publication Data

US 2022/0183853 A1 Jun. 16, 2022

(51) Int. Cl.
| | |
|---|---|
| *A61F 2/44* | (2006.01) |
| *A61F 2/30* | (2006.01) |
| *A61F 2/46* | (2006.01) |

(52) U.S. Cl.
CPC ............ *A61F 2/446* (2013.01); *A61F 2/3094* (2013.01); *A61F 2/4611* (2013.01); *A61F 2002/30143* (2013.01); *A61F 2002/30224* (2013.01); *A61F 2002/30273* (2013.01); *A61F 2002/30385* (2013.01); *A61F 2002/30462* (2013.01); *A61F 2002/30471* (2013.01); *A61F 2002/4677* (2013.01)

(58) Field of Classification Search
CPC ........................ A61F 2/446; A61F 2002/4415
See application file for complete search history.

(56) References Cited

U.S. PATENT DOCUMENTS

| | | | |
|---|---|---|---|
| 4,309,777 | A | 1/1982 | Patil |
| 5,195,541 | A | 3/1993 | Obenchain |
| 6,122,549 | A | 9/2000 | Sharkey et al. |
| 6,126,689 | A | 10/2000 | Brett |
| 6,517,568 | B1 | 2/2003 | Sharkey et al. |

(Continued)

OTHER PUBLICATIONS

Notice of Allowance received for U.S. Appl. No. 16/735,374, mailed on Nov. 17, 2022, 10 pages.

(Continued)

*Primary Examiner* — Julianna N Harvey
(74) *Attorney, Agent, or Firm* — Workman Nydegger

(57) ABSTRACT

A disc implant device can be provided in a generally planar rectangular sheet having a first elongated side, a second elongated side opposing the first elongated side, a first end, and a second end opposing the first end. The generally planar rectangular sheet is structured with alternating segments of joint ridges, each segment of joint ridges being configured to form a spacing joint segment and alternating segments of arm ridges, each arm segment being configured to form a plurality of radially extending arms, the joint segments providing flexibility to the device. When the disc implant is folded or rolled from its planar configuration to a generally cylindrical configuration, the arm segments are axially collapsible and radially expandable such that in such a configuration, the implant includes segments of radially expanded arms separated by spacing joint segments.

17 Claims, 34 Drawing Sheets

(56) References Cited

U.S. PATENT DOCUMENTS

| | | | |
|---|---|---|---|
| 6,558,386 B1 | 5/2003 | Cragg | |
| 6,575,979 B1 | 6/2003 | Cragg | |
| 6,740,090 B1 | 5/2004 | Cragg et al. | |
| 7,621,950 B1* | 11/2009 | Globerman | A61B 17/1637 |
| | | | 623/17.11 |
| 7,959,634 B2 | 6/2011 | Sennett | |
| 8,740,956 B2 | 6/2014 | Smith | |
| 8,845,693 B2 | 9/2014 | Smith et al. | |
| 8,845,728 B1 | 9/2014 | Abdou | |
| 8,979,928 B2 | 3/2015 | Donner | |
| 8,986,318 B2 | 3/2015 | Smith | |
| 9,084,633 B2 | 7/2015 | Smith | |
| 9,421,109 B2 | 8/2016 | Donner et al. | |
| 9,433,511 B2 | 9/2016 | Bagga et al. | |
| 9,486,257 B2 | 11/2016 | Smith | |
| 9,668,775 B2 | 6/2017 | Smith | |
| 9,675,303 B2 | 6/2017 | Choi et al. | |
| 9,724,107 B2 | 8/2017 | Pellegrino et al. | |
| 9,788,967 B2 | 10/2017 | Jo | |
| 9,883,898 B2 | 2/2018 | Smith | |
| 10,058,361 B2 | 8/2018 | Smith | |
| 10,070,926 B2 | 9/2018 | Smith | |
| 10,149,771 B2 | 12/2018 | Dewey | |
| 10,159,475 B2 | 12/2018 | Frey et al. | |
| 10,159,584 B2 | 12/2018 | Carnes et al. | |
| 10,188,526 B2 | 1/2019 | Kuyler | |
| 10,195,524 B2 | 2/2019 | Deridder et al. | |
| 10,219,836 B2 | 3/2019 | Lynch et al. | |
| 10,238,503 B2 | 3/2019 | Branch et al. | |
| 10,258,481 B2 | 4/2019 | Ganter et al. | |
| 10,271,958 B2 | 4/2019 | Schaufler et al. | |
| 10,278,737 B2 | 5/2019 | Smith | |
| 10,285,824 B2 | 5/2019 | Robinson | |
| 10,314,718 B2 | 6/2019 | Suddaby | |
| 10,327,917 B2 | 6/2019 | Glerum et al. | |
| 10,363,142 B2 | 7/2019 | Mcclintock et al. | |
| 10,376,377 B2 | 8/2019 | Seifert et al. | |
| 10,376,380 B2 | 8/2019 | Gamache et al. | |
| 10,376,387 B2 | 8/2019 | Mclean et al. | |
| 10,398,564 B2 | 9/2019 | Overes | |
| 10,398,567 B2 | 9/2019 | Robinson | |
| 10,413,421 B2 | 9/2019 | Arnold et al. | |
| 10,413,424 B2 | 9/2019 | Lewis et al. | |
| 10,426,630 B2 | 10/2019 | Wallenstein et al. | |
| 10,441,430 B2 | 10/2019 | Ludwig et al. | |
| 10,524,819 B2 | 1/2020 | Smith | |
| 10,667,927 B2 | 6/2020 | Amborne et al. | |
| 10,682,240 B2 | 6/2020 | Mcluen et al. | |
| 10,709,574 B2 | 7/2020 | Mcluen et al. | |
| 10,722,380 B1 | 7/2020 | Berry | |
| 10,729,553 B2 | 8/2020 | Bell et al. | |
| 10,758,365 B2 | 9/2020 | Cummins | |
| 10,765,531 B2 | 9/2020 | Kim et al. | |
| RE48,501 E | 4/2021 | Mccormack et al. | |
| 11,020,238 B2 | 6/2021 | Nichols et al. | |
| 11,020,239 B2 | 6/2021 | Miller et al. | |
| 11,033,402 B2 | 6/2021 | Melkent et al. | |
| 11,039,935 B2 | 6/2021 | McAfee | |
| 11,058,547 B2 | 7/2021 | Sharifi-Mehr et al. | |
| 11,602,368 B2 | 3/2023 | Smith | |
| 2001/0049527 A1 | 12/2001 | Cragg | |
| 2002/0016583 A1 | 2/2002 | Cragg | |
| 2002/0095144 A1 | 7/2002 | Carl | |
| 2002/0165550 A1 | 11/2002 | Frey et al. | |
| 2002/0173796 A1 | 11/2002 | Cragg | |
| 2003/0191474 A1 | 10/2003 | Cragg et al. | |
| 2003/0216737 A1 | 11/2003 | Biscup | |
| 2004/0167625 A1* | 8/2004 | Beyar | A61F 2/4657 |
| | | | 623/17.11 |
| 2005/0010205 A1 | 1/2005 | Hovda et al. | |
| 2005/0261695 A1 | 11/2005 | Cragg et al. | |
| 2007/0055260 A1 | 3/2007 | Cragg | |
| 2007/0198021 A1 | 8/2007 | Wales | |
| 2007/0219634 A1* | 9/2007 | Greenhalgh | A61B 17/8858 |
| | | | 623/17.16 |
| 2007/0282443 A1* | 12/2007 | Globerman | A61F 2/4657 |
| | | | 623/17.11 |
| 2008/0208196 A1 | 8/2008 | Daum | |
| 2008/0255563 A1 | 10/2008 | Farr et al. | |
| 2009/0131948 A1 | 5/2009 | Liu et al. | |
| 2009/0171390 A1* | 7/2009 | Sankaran | A61F 2/4455 |
| | | | 623/17.11 |
| 2009/0216234 A1 | 8/2009 | Farr et al. | |
| 2010/0076559 A1 | 3/2010 | Bagga et al. | |
| 2010/0217269 A1 | 8/2010 | Landes | |
| 2010/0331883 A1 | 12/2010 | Schmitz et al. | |
| 2011/0054538 A1* | 3/2011 | Zehavi | A61F 2/4455 |
| | | | 606/279 |
| 2011/0093072 A1* | 4/2011 | Siegal | A61F 2/4611 |
| | | | 623/11.11 |
| 2011/0118789 A1* | 5/2011 | Siegal | A61B 17/1796 |
| | | | 606/279 |
| 2011/0118840 A1 | 5/2011 | Huntsman et al. | |
| 2011/0245926 A1* | 10/2011 | Kitchen | A61F 2/4465 |
| | | | 623/17.16 |
| 2011/0270396 A1* | 11/2011 | Leibowitz | A61F 2/4611 |
| | | | 623/17.11 |
| 2013/0006232 A1 | 1/2013 | Pellegrino et al. | |
| 2013/0103103 A1 | 4/2013 | Mire et al. | |
| 2013/0178940 A1 | 7/2013 | Farley | |
| 2015/0025514 A1 | 1/2015 | Carl | |
| 2016/0302936 A1 | 10/2016 | Billon et al. | |
| 2017/0348034 A1 | 12/2017 | Lapierre et al. | |
| 2019/0008654 A1* | 1/2019 | Thommen | A61F 2/4611 |
| 2020/0138466 A1 | 5/2020 | Smith | |
| 2021/0121301 A1 | 4/2021 | Faulhaber et al. | |
| 2021/0128919 A1 | 5/2021 | Zellmer et al. | |
| 2021/0137685 A1 | 5/2021 | Kahmer et al. | |
| 2021/0137701 A1 | 5/2021 | Miller et al. | |
| 2021/0137702 A1 | 5/2021 | Neubardt | |
| 2021/0145600 A1 | 5/2021 | Sharifi-Mehr et al. | |
| 2021/0153909 A1 | 5/2021 | Siby-Kurian et al. | |
| 2021/0154023 A1 | 5/2021 | Picha et al. | |
| 2021/0154365 A1 | 5/2021 | Sohn et al. | |
| 2021/0170187 A1 | 6/2021 | Compton et al. | |
| 2021/0177603 A1 | 6/2021 | Dewey et al. | |
| 2021/0177618 A1 | 6/2021 | Branch et al. | |
| 2021/0196480 A1 | 7/2021 | Fabian, Jr. | |
| 2021/0205046 A1 | 7/2021 | Metcalf et al. | |
| 2021/0205093 A1 | 7/2021 | Deshpande | |
| 2021/0205097 A1 | 7/2021 | Spann | |

OTHER PUBLICATIONS

Restriction Requirement received for U.S. Appl. No. 16/735,374, mailed on Aug. 24, 2022, 7 pages.

Final Office Action received for U.S. Appl. No. 15/255,679, mailed on Mar. 25, 2019.

Notice of Allowance received for U.S. Appl. No. 15/255,679, mailed on Aug. 21, 2019.

Office Action received for U.S. Appl. No. 15/255,679, mailed on Dec. 5, 2018.

U.S. Appl. No. 16/735,374, filed Jan. 6, 2020.

* cited by examiner

STEP 1

300

STEP 2

STEP 3

STEP 4

STEP 5

STEP 6

STEP 8

STEP 9

STEP 10

STEP 13

STEP 14,15,16

STEP 17

STEP 20

STEP 22

STEP 24

314

322

324

326

300

STEP 25-29

320

332

EXPANDABLE INTERBODY FUSION DEVICE FOR USE WITH POSTERIOR TO LATERAL APPROACH

CROSS-REFERENCE TO RELATED APPLICATIONS

The present application incorporates by reference U.S. patent application Ser. No. 16/735,374, filed Jan. 6, 2020, which claims the benefit under 35 USC § 119(e) of U.S. patent application Ser. No. 62/956,995, filed Jan. 3, 2020 and entitled "POSTERIOR TO LATERAL APPROACH". U.S. patent application Ser. No. 16/735,374 is also a continuation-in-part of U.S. patent application Ser. No. 15/255,679 filed Sep. 2, 2016, now U.S. Pat. No. 10,524,819, which claims the benefit under 35 USC § 119(e) of U.S. patent application Ser. No. 62/370,928, filed Aug. 4, 2016 and entitled "POSTERIOR TO LATERAL APPROACH"; U.S. patent application Ser. No. 62/382,007, filed Aug. 31, 2016 entitled "POSTERIOR TO LATERAL APPROACH"; U.S. patent application Ser. No. 62/270,013, filed Dec. 20, 2015 and entitled "POSTERIOR TO LATERAL APPROACH FOR INTERBODY SPINAL FUSION"; and U.S. patent application Ser. No. 62/214,489, filed Sep. 4, 2015 and entitled "EXPANDABLE INTERBODY FUSION DEVICE". The disclosure of each of the foregoing is herein incorporated by reference in its entirety.

BACKGROUND OF THE INVENTION

1. The Field of the Invention

The present invention generally relates to methods for accessing one or more discs of the vertebrae, e.g., as part of a spinal interbody fusion, as well as implant devices for use therewith.

2. The Relevant Technology

Over the past several decades, spinal surgery has increasingly become an important option available to surgeons and patients in treating issues related to the spine. Because the spine generally provides support and movement for the body, a problem with the spine (e.g., a back disorder) can disrupt even the simplest life activities. In general, thousands of surgical interbody fusions of the spine are performed each year in an attempt to decrease pain and to increase function for the patient. Interbody fusion is a common procedure that attempts to create a bony bridge, or union, between two vertebral bodies to eliminate movement between the two individual vertebrae. This loss of motion can be curative for those suffering from a variety of back disorders, including degenerative conditions or instabilities.

Many different methods are currently in use by surgeons to accomplish interbody fusion. Generally, an incision is made, the disc is exposed, and the disc material is removed. The end plates of the vertebral bodies may be stripped of any remaining cartilage thus exposing the bony faces of the adjacent vertebrae. The disc space may be filled with a material compatible with fusion. In most cases, the disc space may also be filled with some sort of implant, or spacer, intended to prevent narrowing, filling, or collapse of the disc space during or after the fusion process. Generally speaking, the greater the agitation, scraping, or other "damage" to the vertebral endplates, the greater the biologic efforts effected by the body to heal the damage, thus creating the fusion. Current approaches used by spinal surgeons to access the disc space and accomplish an interbody fusion typically include anterior, posterior, posterolateral, or a lateral approach.

Surgical techniques currently available are reliable, but they are not without risk and potential complications. Reducing risk without reducing the effectiveness of the surgery is desirable. In addition, it would be advantageous if new techniques better limited the amount of surgical trauma to the patient, reducing recuperation and healing times. As such, there exists a continuing need for improved techniques for performing interbody spinal fusion. In addition, once the disc space has been accessed (by whatever technique), there is a need for an implant device that can fill the disc space.

BRIEF SUMMARY

In one aspect, the present invention relates to a disc implant device, as well as systems and methods for inserting the disc implant device into a patient's disc. For example, an example of the inventive disc implant device can include a body comprising a series of generally cylindrical arm segments, each generally cylindrical arm segment being separated from an adjacent arm segment by a joint segment, each arm segment including a plurality of rising arm members and a plurality of falling arm members such that the body comprises alternating joint segments and arm segments. A compliant hinge mechanism structure is provided between each rising arm member and each falling arm member, so that when a given arm segment of the disc implant device is axially collapsed and radially expanded along the compliant hinge mechanism structure, a plurality of radially extending arms are formed in each arm segment of the body. Adjacent arm segments are separated from one another by a joint segment. The implant device may include any desired number of arms per arm segment, e.g., from 3 to 12, or otherwise. In an embodiment, 6 to 8 arms may be provided per arm segment. The generally cylindrical arm segment may therefore more accurately have a polygonal cross section (e.g., such as a hexagonal or octagonal cross section).

In an embodiment, such an implant device body may be formed from an initially generally rectangular, generally planar sheet in an initial as manufactured configuration, e.g., having a first elongated side, a second elongated side opposing the first elongated side, a first end, and a second end opposing the first end. The generally horizontal and planar rectangular sheet comprises alternating joint segments configured to form a plurality of spacing joints, alternated with arm segments, which arm segments are configured to be radially expandable and axially collapsible to form a plurality of radially extending arms once the sides of the body are rolled or folded towards one another (transforming the planar configuration into a generally cylindrical configuration). The joint segments may be configured to provide flexibility to the disc implant device when the disc implant device is in its generally cylindrical configuration. The joint segments and arm segments alternate, such that each joint segment is disposed in between two adjacent sections of arm segments.

In one aspect, the present invention relates to methods for forming a disc implant device. e.g., from such an initially planar, rectangular sheet structure. Although a sheet structure represents one configuration in which the disc implant device may initially be manufactured (e.g., through machining, injection molding, stamping, 3D printing, etc.) It will be appreciated that the disc implant device is not limited to manufacture in such a planar sheet configuration, but could be formed to already include the generally cylindrical configuration (e.g., 3D printed or otherwise formed in such configuration). By way of example, one method may include obtaining a disc implant device comprising a generally horizontal rectangular sheet having a first elongated side, a second elongated side opposing the first elongated side, a first end, and a second end opposing the first end, the disc implant device comprising alternating sections of joint segments and arm segments configured to form a plurality of radially extending arms, as described.

The disc implant device (i.e., the generally horizontal rectangular sheet) is folded or rolled such that the first elongated side is pulled flush or adjacent with the second elongated side, such that the disc implant comprises a generally cylindrical shape. As noted above, in an embodiment, the disc implant device can be manufactured in such a generally cylindrical shape configuration. In the generally cylindrical configuration, the arm segments can be axially collapsed, forcing the arm members of each arm segment to expand out radially. In other words, the generally cylindrical shape is axially compressible or collapsible such that the first end is brought toward the second end (shortening the overall device length, as well as the length of each arm segment, but expanding the radial width of each arm segment). The disc implant device comprises a plurality of joint segments and a plurality of arm segments, in an alternating arrangement, along the length of the device. Each of the first and second ends may include half of a joint segment structure, connecting the adjacent terminal arm segment arm members to one another.

In one aspect, the present invention relates to methods for inserting a disc implant device into a disc of a patient's vertebrae of a patient's spine as part of a discectomy or spinal interbody fusion. For example, a guide wire is secured at or near a lateral aspect of an emptied disc space of the disc, wherein the guide wire follows a predetermined path that begins as a posterior or posterolateral approach to the disc. A beneficial posterior to lateral approach as developed by Applicant is described in the Patent Application numbers already referenced above. In some instances, said path is curved to allow for the posterior to lateral approach. After the guide wire is secured, the disc implant device is threaded onto the guide wire. In some instances, the disc implant is configured in its folded, generally cylindrical configuration when threaded onto the guide wire. In an embodiment, it can be beneficial to pass the disc implant device through the associated instrumentation (e.g., cannula, etc.) with the implant device in its folded generally cylindrical configuration (i.e., a series of generally cylindrical arm segments separated by joint segments). While being advanced, the arm segments of the device may not be in their axially collapsed, radially extended configuration, so as to more easily fit within the cannula or other instrumentation space used to access the disc space. Axial collapse and radial expansion may occur only once the implant enters the disc space to be filled.

Once the disc implant device is threaded onto the guide wire, a leading end of the disc implant is inserted into a posterior or posterolateral surface of the patient's back at a start of the predetermined path. The disc implant device is then advanced along the predetermined path (e.g., as defined by the path of the guide wire) which deviates from a posterior or posterolateral orientation towards a lateral orientation relative to the disc as the disc implant advances from a posterior or posterolateral surface through the psoas muscle of the patient until it has reached or nearly reached a lateral aspect of the disc. Details of such an approach, and cleaning or preparation of the disc space are described in various others of Applicant's applications, already incorporated by reference. Once the disc implant device is located in the desired location within the patient's disc, the disc implant is axially collapsed and radially expanded into its deployed configuration, with the arm members of the arm segments extending radially outward. The disc implant is lodged inside the emptied disc space of the disc and comprises a plurality of radially extending arms in each arm segment, separated by a plurality of joint segments, providing filling and support within the disc space, to prevent future unwanted collapse of the disc.

Such radial expansion of the arm segments can be accomplished using any desired mechanism or technique. For example, a stop (e.g., zip tie) may be provided at end(s) of the guidewire, allowing a practitioner to move the stop along the guidewire, collapsing each arm segment as the stop is progressively advanced towards the other end of the guide wire (e.g., towards the disc end of the guide wire). Alternative mechanisms for radial expansion may include a rivet system, a notch in the guide wire (e.g., a snap), use of a screw, or the like. Various methods of axially collapsing and radially expanding the implant body structure as described herein will be apparent to those of skill in the art, any of which are within the scope of the present disclosure.

While the posterior to lateral approach may be principally described herein, it will be appreciated that the present disc implant devices can be used with any desired approach (e.g., anterior, lateral, or otherwise). In addition, while the implant devices are described principally for use in filling a disc space as part of a discectomy or spinal interbody fusion, it will be appreciated that the present implant devices may be useful in other implantation locations, where a space within a bone or the like needs to be filled.

In Applicant's novel posterior to lateral approach, the disc location is accessed directly laterally, or nearly directly laterally (e.g., some angular offset from directly lateral may be acceptable) after an initial entry from the posterior surface (i.e., the back) of the patient. Such an approach may also be referred to as a radial approach, e.g., a radial interbody fusion. According to one embodiment, one such method may include inserting a leading end of a tool (e.g. a cannula) into the patient's back at a location on the posterior surface that is laterally offset from a patient's midline (e.g., midline and spinous process). The tool may begin with an initial entry into the patient from a posterior (or perhaps more accurately posterolateral) approach relative to the disc. The tool may continue to be advanced along a path which may begin to deviate from the posterior (or posterolateral) approach towards a lateral approach as the tool is advanced toward a lateral aspect of the disc. When the leading end of the tool actually reaches the disc location, it may access the disc location from a location that is lateral relative to the disc location. The tool may be used to access the disc location, to remove disc material, to deliver a cutting tool for removing the disc material, and other steps associated with the spinal interbody fusion procedure performed from a lateral perspective, including inserting a disc implant device as described herein.

A posterior to lateral approach has several distinct advantages because it may mitigate some risks associated with other approaches typically used in spinal interbody fusion procedures. For example, an anterior approach requires retraction of a peritoneal sac and large blood vessels (e.g. left common iliac vein) in order to access the disc. Access to the lumbar disc is difficult using a posterior approach because the patient's spinal canal, including the contained nerve roots, other structures, and bone of the patient (including the facet joints) block easy access to the disc. As a result, lamina must be removed and nerve roots retracted before the disc can be accessed. A lateral approach initially presents a risk to a patient's colon, which must be carefully bypassed to access the disc. The posterior to lateral approach described herein is designed to avoid damage and risk to these structures. For example, the posterior to lateral approach may be performed in a manner so that the pathway only passes through the patient's skin and muscle (e.g., psoas muscle) to access the disc, making the approach potentially much less invasive, while maintaining the advantages of accessing the disc and eventually inserting the disc implant device into the disc space from a lateral perspective.

Because the posterior to lateral approach may be less invasive, only passing through muscle tissue, which can easily be parted to one side or the other, without necessarily cutting or damaging the muscle, the healing time for a patient undergoing spinal interbody fusion using the posterior to lateral approach may be far less than other available approaches. In fact, for many patients such a procedure may be performed on an outpatient basis. A capture tool may remain secured to stabilize the end of the guide wire, and prevent it from migrating, until the insertion process has been completed. Stabilizing the end of the guide wire in this or a similar manner may prevent the wire from migrating and keep the disc implant device from deviating from a path desired by the practitioner.

The present disc implant devices are also advantageous, as they provide a configuration during travel to the disc location where the implant device is defined by a relatively small radius (smaller than that of the disc space to be filled), where the body of the implant device is defined by a generally cylindrical structure that is flexible and pliable, as it is passed through the delivery pathway, to the disc space entrance. Also advantageously, once the implant device reaches the disc space, each segment of arm members and each joint segment can be sequentially inserted into the space in this low profile, streamlined configuration, and then once a given arm segment is in the disc space, it can be radially expanded to fill the disc space.

Such configurations do not necessarily rely on any shape memory alloy (e.g., a nitinol alloy), large coils, or other structure to fill the space, but the implant capability to switch from the low profile streamlined delivery configuration (generally cylindrical) to the radially expanded configuration is possible because of the structure of alternating joint segments and arm segments, each of which can be easily and simply pulled or pushed between the two configurations. In an embodiment, the implant device may be formed from a suitable implant material, such as titanium, a titanium alloy, stainless steel, PEEK, another suitable implantable polymer, or the like. In an embodiment, the implant may be formed entirely from a single material (e.g., Ti-6A1-4V titanium alloy).

These and other advantages and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 26B shows a close up of a portion of the device shown in FIG. 26A.

DETAILED DESCRIPTION OF THE PREFERRED EMBODIMENTS

I. Introduction

Figure 1:
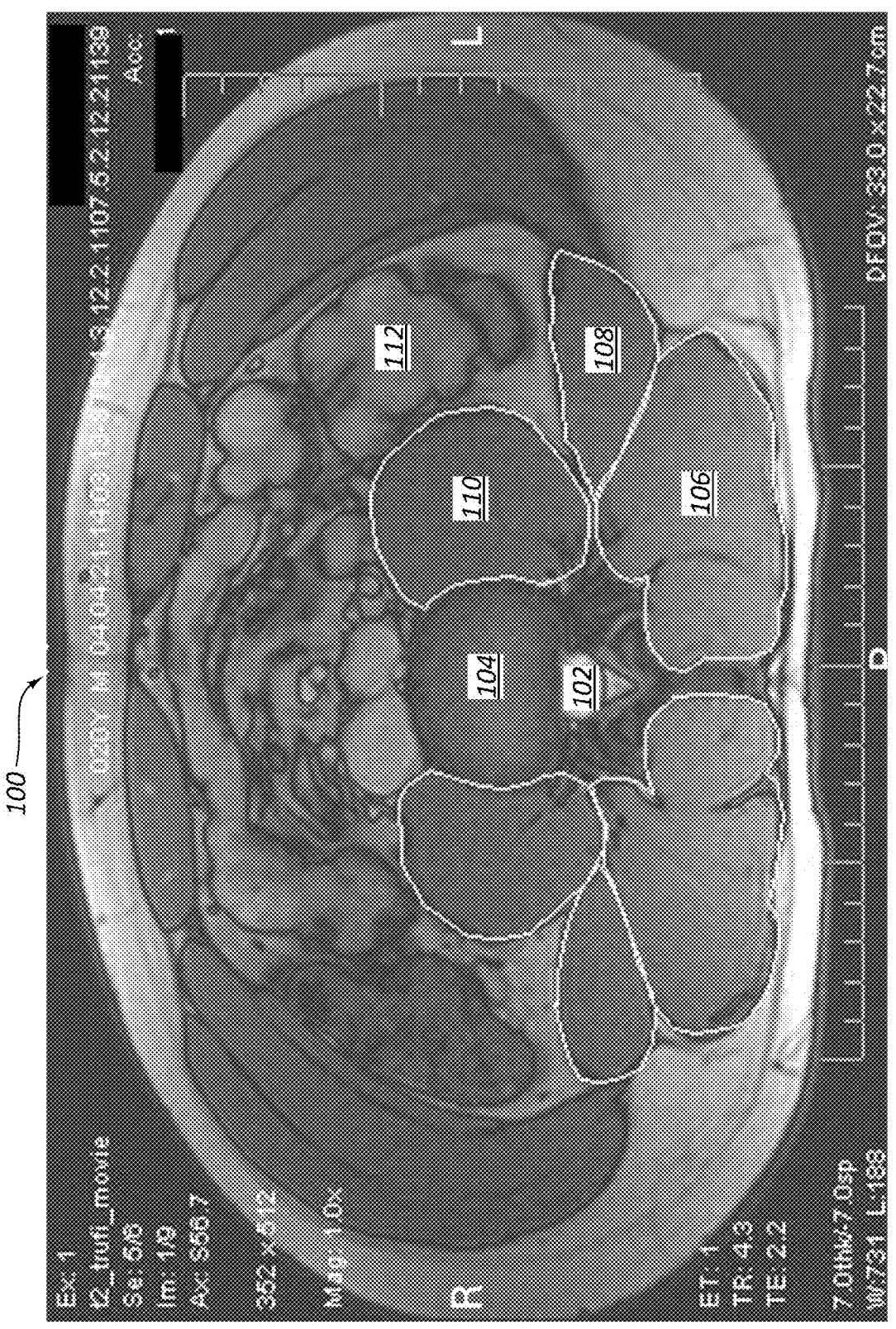
FIG. 1 is a cross-sectional scan through a patient's body, showing the various structures near the vertebrae and disc to be fused.

The present invention relates to disc implant devices, methods for their use, and manufacture. For example, a disc implant device can be provided in a form having a body comprising a series of generally cylindrical arm segments, each generally cylindrical arm segment being separated from an adjacent arm segment by a joint segment, each arm segment including a plurality of rising arm members and falling arm members, so that the body comprises alternating joint segments and arm segments, wherein the arm segments include a compliant hinge mechanism structure between each rising arm member and each falling arm member, so that each arm segment is configured to form a plurality of radial arms when a given arm segment is axially collapsed and radially expanded along the compliant hinge mechanism structure, such that the plurality of radial arms form one or more sets of radially extending arms, adjacent segments of radial arms being separated from one another by a joint segment. While described generally with compliant hinge mechanism structures, it will be appreciated that an alternative configuration could be formed using hinge pins. Furthermore, each segment could be a stand along segment, without a hinge therebetween (e.g., similar to a string of beads).

While not necessarily limited to such, the implant body can be formed from an initially generally planar sheet of material, so as to have a plurality of joint segments and a plurality of arm segments, all of which are in the same planar sheet once manufactured. Such a configuration may be 3D printed, laser cut, cut by water-jet, machined by wire, CNC machined, or any other suitable formation technique. Although the body can be manufactured in the form of a planar sheet, the disc implant device body is configured to be folded or rolled into a cylindrical shape by rolling or folding the opposed elongate sides of the body towards one another. When in such a cylindrical rolled configuration, the arm segments are also axially collapsible when a first end of the disc implant device (or first end of a given arm segment) is subsequently compressed toward a second end of the disc implant device (or s second end of a given arm segment). Whether manufactured in a flat planar sheet configuration or not, the implant body can be provided to the practitioner in this generally cylindrical configuration, where the arm segments are ready for axial collapse and radial expansion. The axially collapsed, radially expanded configuration of the disc implant device includes a plurality of joint segments, which define and allow for flexibility and curvature of the generally cylindrical disc implant device (e.g., allowing it to assume a straight or curved configuration, like a string of sausage links). In addition to the joint segments, the implant device also includes a plurality of arm segments, each including a plurality of rising arm and falling arm members, with a compliant hinge mechanism structure or hinge pin between each rising and falling arm member. Such a configuration allows each arm segment to axially collapse, and radially expand, to provide support inside a cleared disc space once placed.

The present invention relates to systems and methods for inserting a disc implant device into a disc space of a patient as a part of an interbody fusion procedure, as well as to tools used for clearing the disc space of the patient between vertebral endplates of the vertebrae as a part of such an interbody fusion. Such a method may include inserting a leading end of the disc implant device (e.g., through a cannula) into the patient's back at a location on the posterior surface that is laterally offset from a patient's midline (e.g., spinous process). The disc implants device's initial entry into the patient may be from a posterior approach relative to the disc (although laterally offset as described in Applicant's earlier applications, referenced above, so as to perhaps most accurately be described as posterolateral). As the disc implant device is advanced along its designated path towards the lateral aspect of the disc, the path deviates from a posterior approach towards a lateral approach to the disc (e.g., the approach pathway is curved). When the leading end of the disc implant device actually reaches the disc location, it may be inserted into the disc space from a location that is lateral (or substantially lateral) relative to the disc. Prior to placement of the disc implant device, this same approach and associated instrumentation is used to access the disc location, to deliver a cutting tool for removing the diseased or other desired material in the disc space, actually remove the diseased or other desired disc material, etc., prior to inserting the disc implant device. The implant device makes the approach to the disc space in its generally cylindrical configuration (i.e., resembling a series of sausage links (the arm segments) tied together (by the joint segments). Once a given arm segment has reached the disc space, it can be radially expanded, substantially filling the height of the disc space (e.g., a 22 mm height)

As used herein, reference to a compliant hinge mechanism refers to a flexible mechanism that achieves force and motion transmission through elastic body deformation, e.g., due to the location of the hinge being significantly thinner than the surrounding structures. Such compliant hinge mechanisms will be apparent to those of skill in the art. Such structures gain their ability to flex or bend from the relative flexibility of the structure itself, rather than from rigid-body joints. Such structures may be jointless, formed from a single piece of material across the compliant mechanism.

a. Exemplary Methods and Devices

FIG. 1 shows a cross-sectional scan through a torso portion of an exemplary patient's body 100, showing the various structures near the vertebrae 102 and disc 104 to be fused. Some of the illustrated structures include the muscles 106, 108, and 110 surrounding the vertebrae 102. Specifically, the muscles may include the erector spinae 106, the quadratus lumborum 108, and the psoas major 110 muscles. The scan also shows the colon 112. Although described principally in reference to the right side of the scan, it will be appreciated that an analogous posterior to lateral approach may be possible from the left side, with often symmetrical muscle and other structures present.

Figure 2:
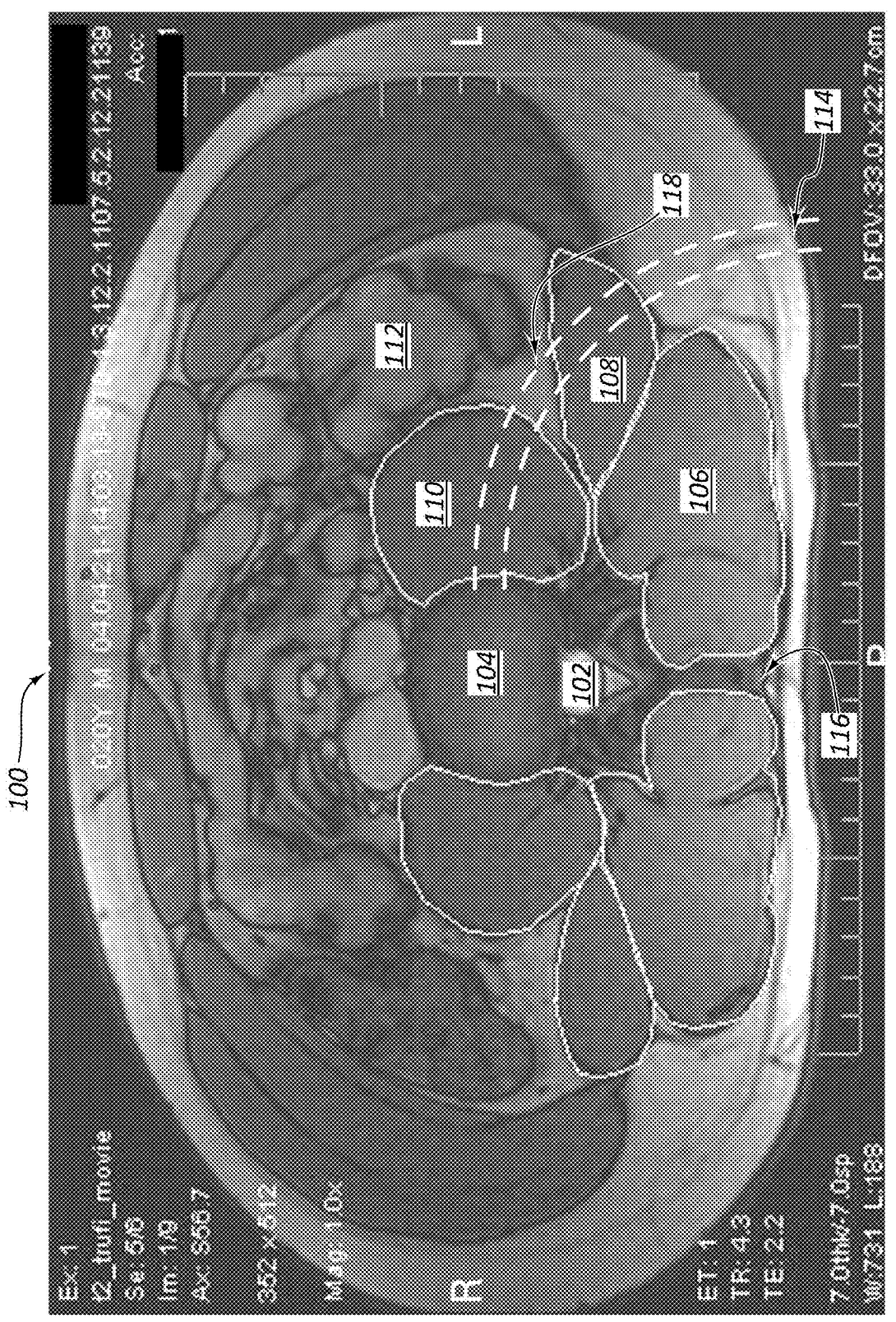
FIG. 2 shows the scan of FIG. 1, illustrating an exemplary posterior to lateral approach to the disc, reducing risks to adjacent structures as compared to a posterior approach, or a lateral approach.

FIG. 2 illustrates an exemplary posterior to lateral approach to the disc 104, overlaid on the scan of FIG. 1. As shown, the entry site 114 may be on a posterior surface of the patient's back at location that is laterally offset from a patient's spinous process 116. The path 118 to the disc 104 may begin as a posterior approach (perhaps most accurately, "posterolateral approach") relative to the disc 104, but as the path 118 advances, it may deviate from such approach towards a lateral approach. Therefore, when the path 118 reaches the disc 104, it may reach a lateral aspect of the disc 104.

While FIG. 2 shows the path 118 passing through the quadratus lumborum 108 and psoas major 110 muscles, while avoiding the colon 112, it will be appreciated that the posterior to lateral approach is not limited to passage through those specific muscles. Depending on the structure of the patient's back muscles and the type of tool used to access the disc 104, the path 118 may be through any of the three major back muscles surrounding the vertebrae 102. Those of skill in the art will also appreciate that a muscle's fibers, as living tissue, may be parted from one another, rather than cut, to allow relatively easy passage through the muscles. By avoiding cutting the muscles, the patient may recover significantly more quickly from the interbody fusion procedure. For example, it may be possible to perform such a procedure on an outpatient basis, with much faster recovery of the patient to normal activities.

As shown, the entry site 114 may be a location on the posterior surface of a patient's back that is laterally offset from a patient's spinous process 116. The path 118 to the disc 104 may initially be a posterior approach relative to the disc 104, but as the path 118 advances, it may deviate from a posterior approach towards a lateral approach. This allows the approach to avoid having to tunnel through or around the sensitive and delicate structures associated with the spinal canal, spinal cord, other nerves, and bone of the patient typically encountered in a posterior approach or traditional posterolateral approach. In addition, this approach reduces the dangers to the colon inherent in a strict lateral approach. Injuries to the lumbar plexus can be limited ty eliminating the need for additional retraction as is used in lateral approaches. The posterior to lateral approach which takes a non-linear route to the disc 104 advantageously traverses mostly, if not substantially entirely through muscle tissue.

Such a route greatly minimizes risk to the sensitive organs and other structures of the patient, while also greatly minimizing damage to the patient that must be healed during recovery.

Figure 3:
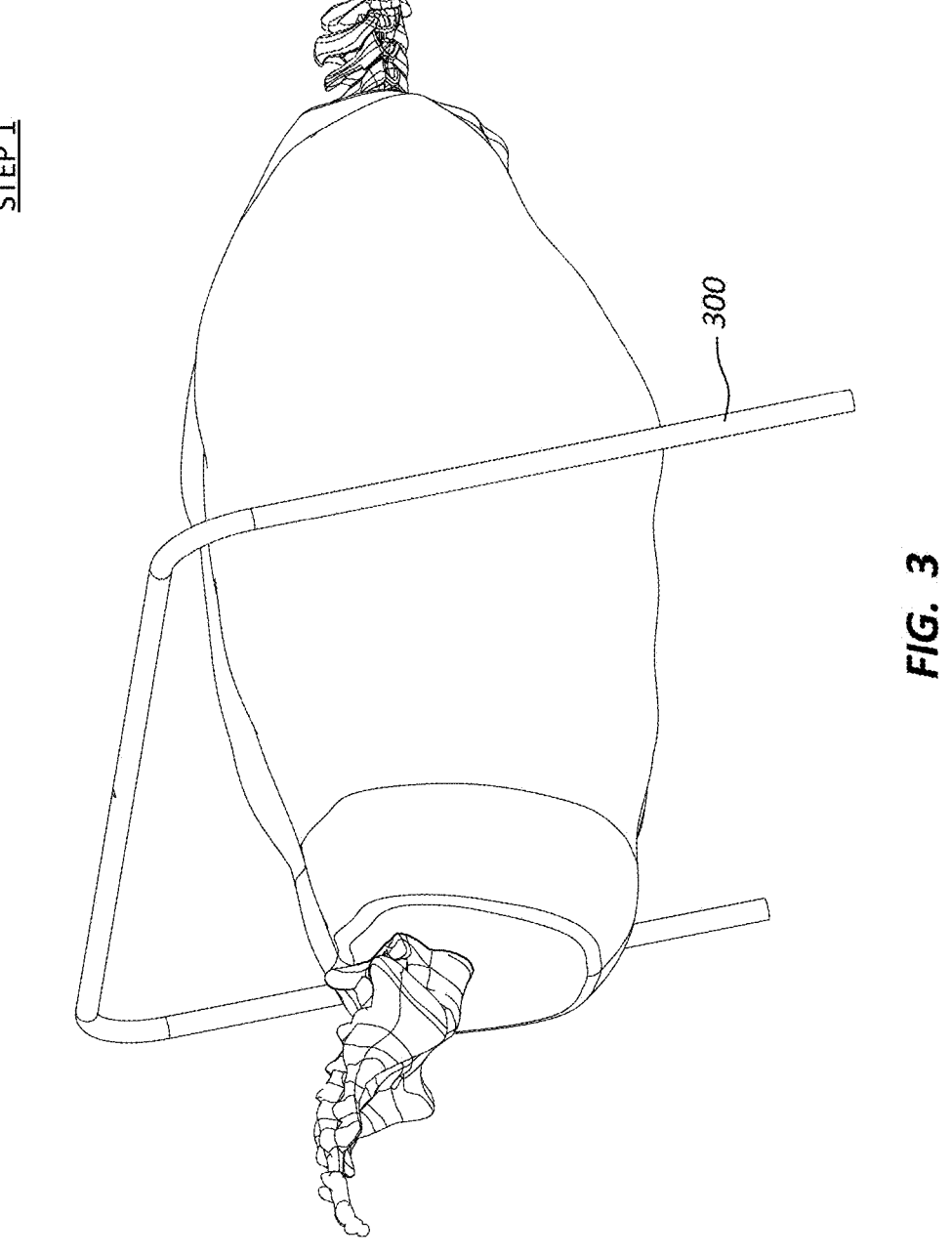
FIGS. 3-25 illustrate progressive steps of an exemplary posterior to lateral approach procedure.
Figure 4:
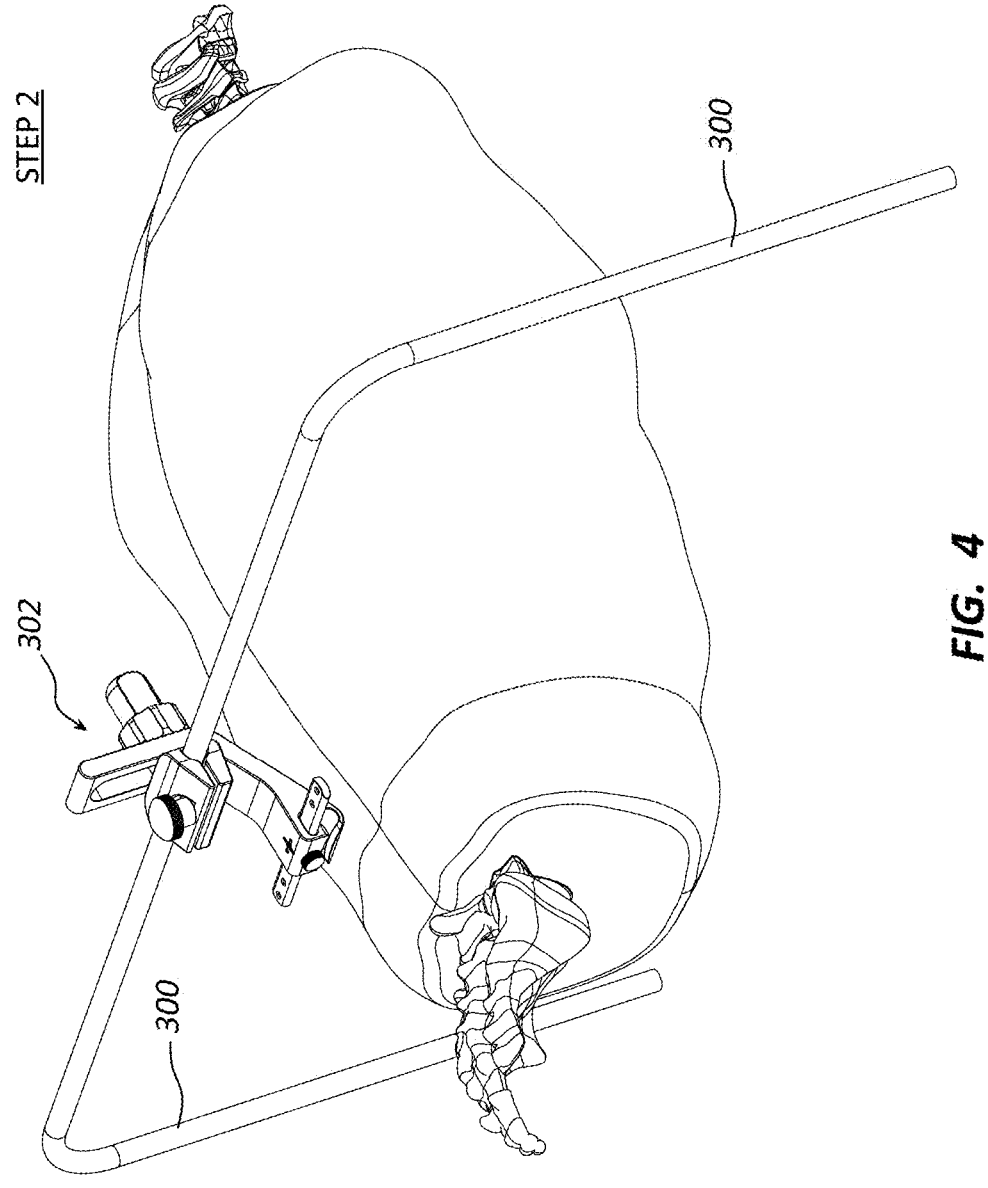
Figure 5:
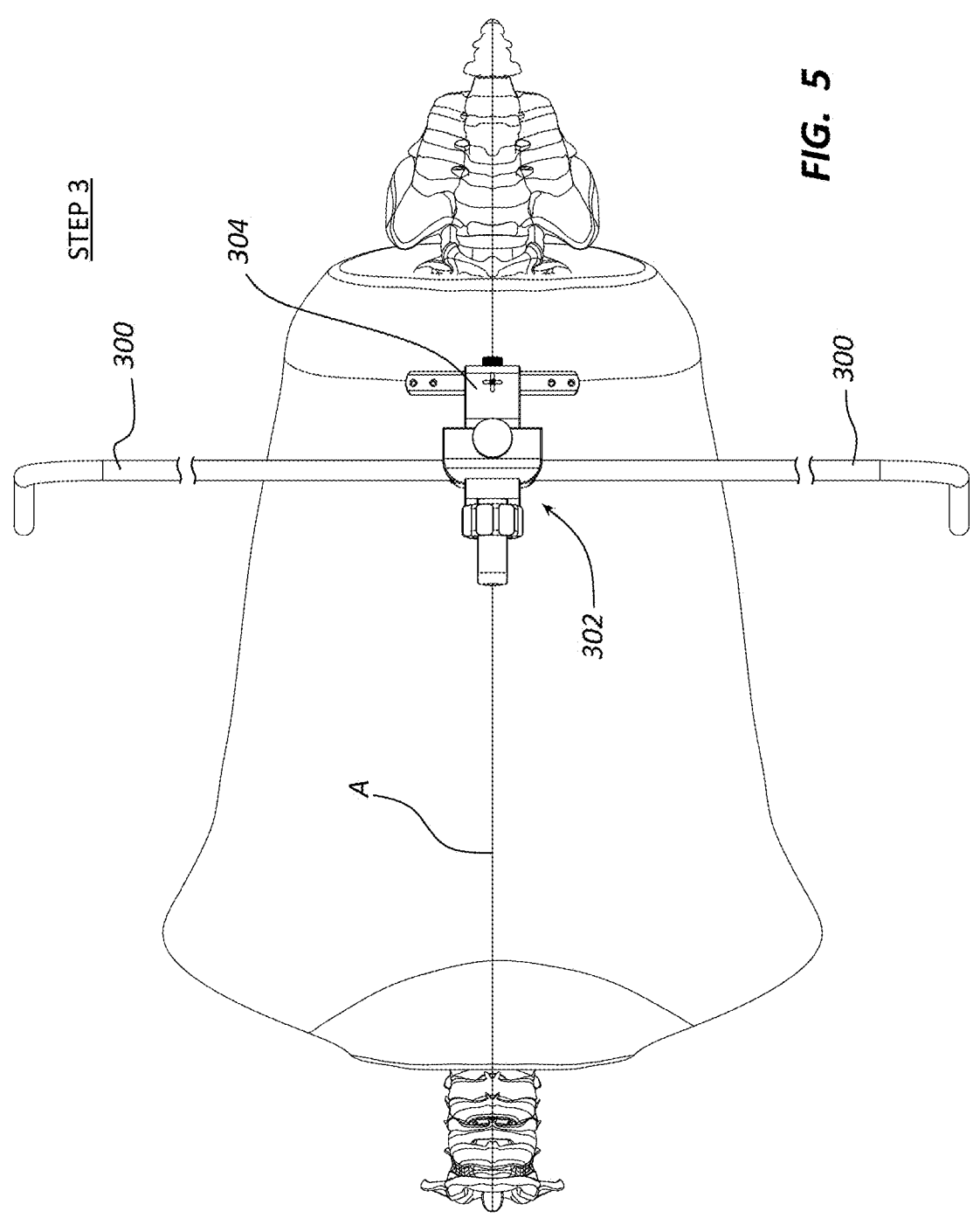
Figure 6:
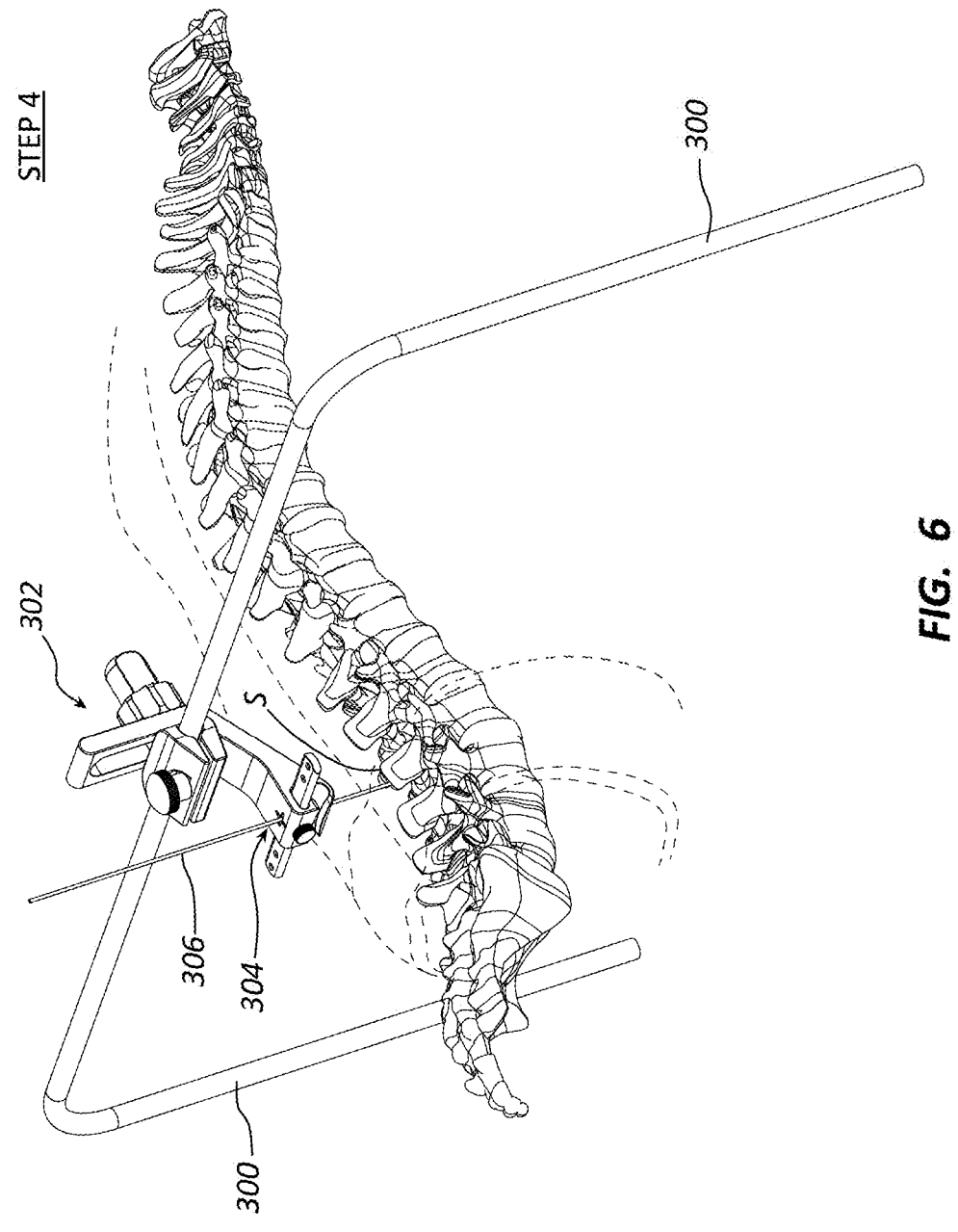
Figure 7:
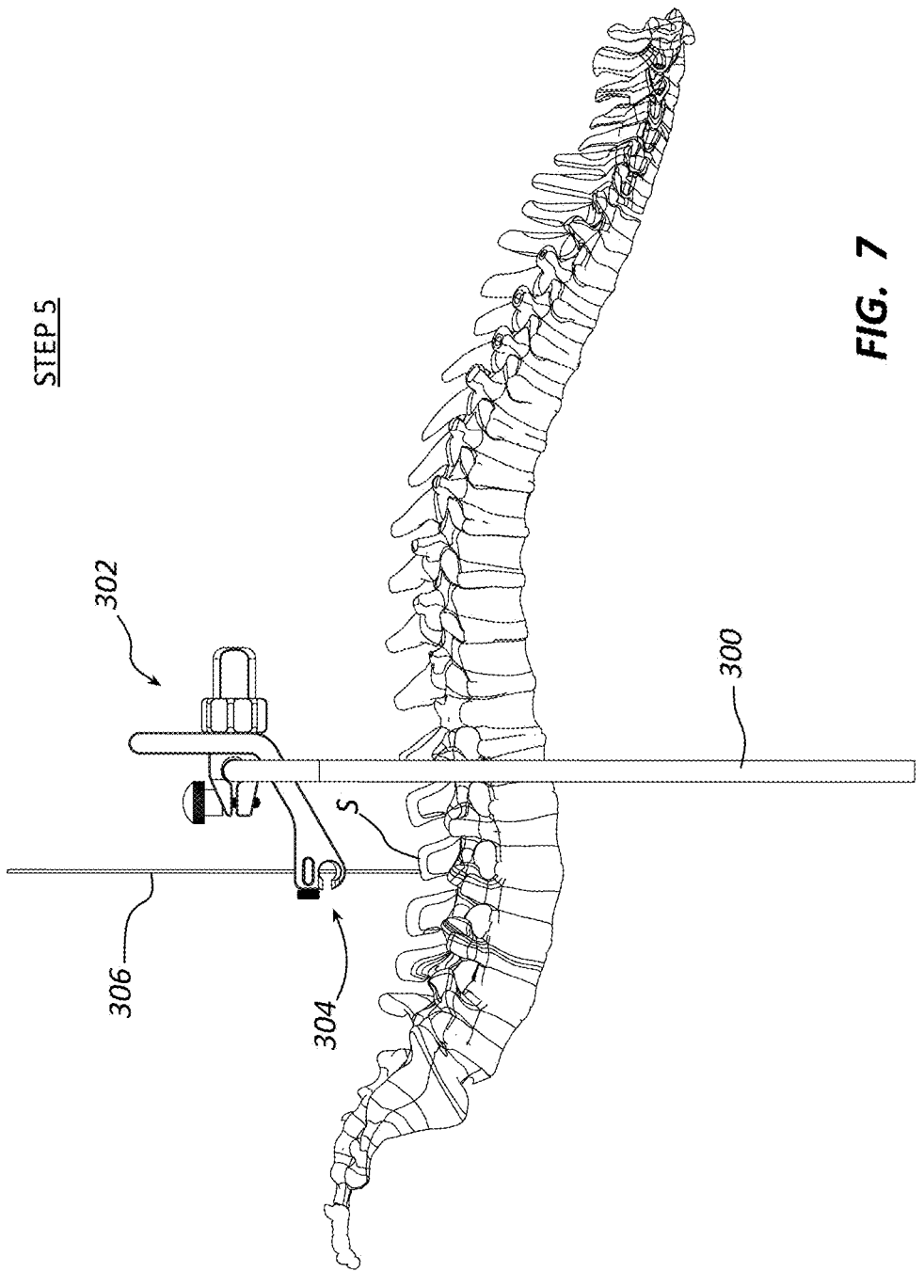

FIGS. 3-25 illustrate progressive steps for an exemplary posterior to lateral approach. FIG. 3 shows how crossbar 300 may be attached to the bed or operating table (not shown), securing the system in place relative to the patient on which the procedure is being performed. As shown in FIG. 4, rod insertion guide 302 is attached to the crossbar 300. FIG. 5 shows how the midline marker 304 on rod insertion guide 302 is adjusted to be aligned with the patient's midline (i.e., longitudinal axis "A"). As shown in FIG. 6, a dropwire 306 can be inserted through the midline marker 304, and passed through the skin of the patient, to the level of the spinous process "S" of the disc where the spinal fusion or other process is to be performed. As shown in FIG. 7, the angle of dropwire 306 can be compared to the angle of the disc space "D" (see FIG. 10) being addressed. The rod insertion guide 302 can be adjusted so that the angle of dropwire 306 matches that of the disc being addressed (i.e., operated on). The distance between the spinous process "S" and the skin can also be noted, as described in patent application Ser. No. 16/735,374, herein incorporated by reference in its entirety. Using a relatively simple calculation, the height "H" to place rod insertion guide 302 above the patient's skin can be determined by subtracting the measured distance from the center of the disc to the spinous process "S" (taken from the CT scan), and the additional distance between the spinous process and the skin surface from twice the radius of the curved tool (e.g., rod) 314 to be used, as in the calculation below.

$$H = 2R - CTDSP - SSP$$

Where H is the height at which the rod insertion guide 302 is to be placed above the patient's skin, R is the radius of the curved rod 314, CTDSP is the CT scan measured distance from the center of the disc to the spinous process "S", and SSP is the distance between the spinous process "S" and the skin.

Figure 8:
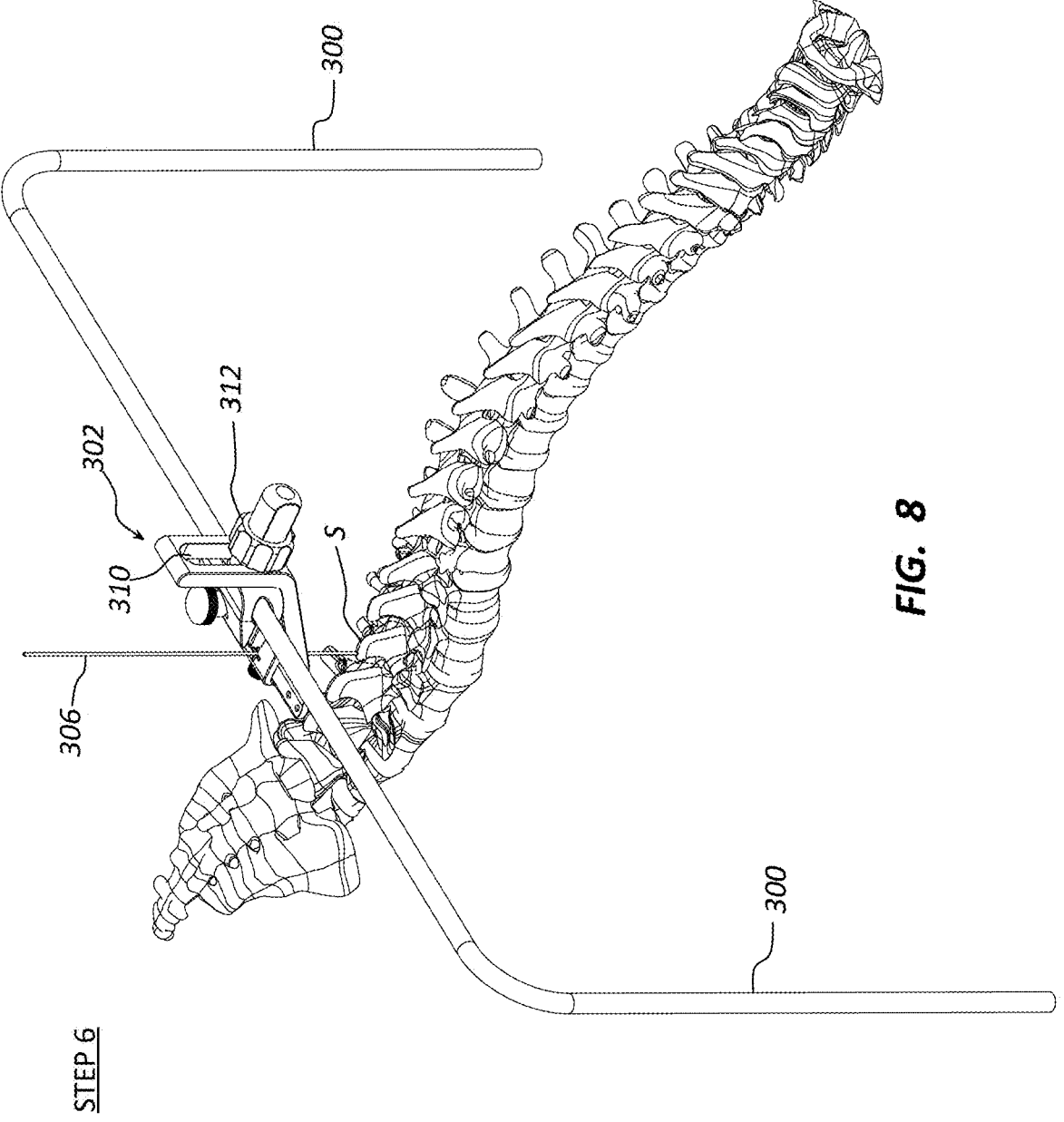
Figure 9:
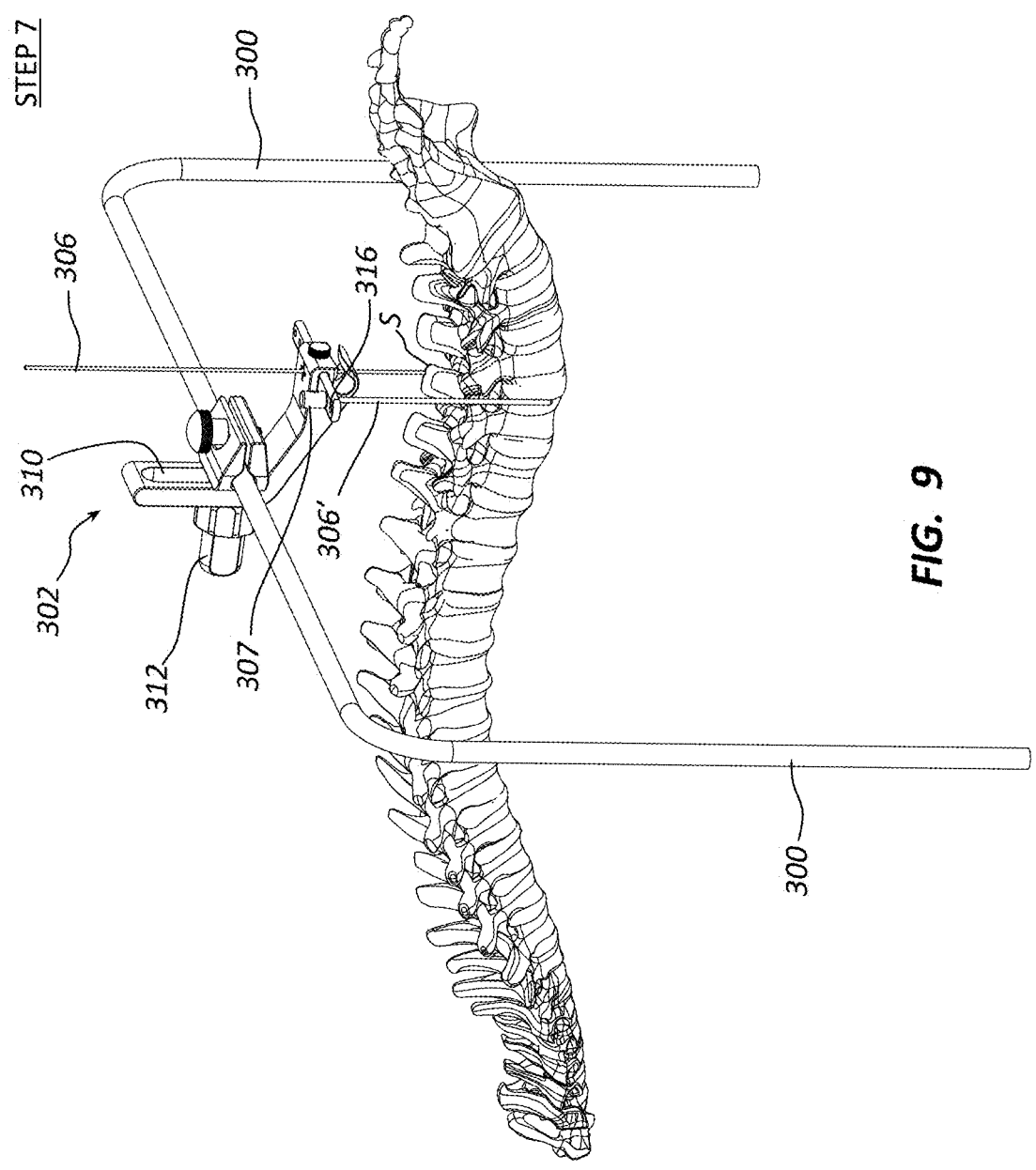

As shown in FIG. 8, rod insertion guide 302 can be adjusted up or down as needed, to ensure that the midline distance from the center of the disc space to the center of the curved rod path is approximately equal to twice the radius of the curved rod 314 to be used. Such up and down adjustment can be achieved using the slot and knob arrangement 310 and 312 respectively, as shown. It will be apparent that numerous other arrangements can also be suitable for making such an adjustment, and such are within the scope of the present disclosure. As shown in FIG. 9, a second rod (e.g., a confirmation rod) 306' can be inserted through one or more provided confirmation rod holes 316 in rod insertion guide 302 (e.g., laterally offset from the midline marker hole 304). As shown, more than one such hole 316 may be provided, at different lateral distances from the centerline hole 304 to accommodate different skeletal or other patient geometries. Rod 306' can be advanced through the skin and soft tissues, until the top portion of confirmation rod 306' is seated in the base of the confirmation rod hole 316. For example, where rod 306' includes an enlarged head 307 as shown, this can act as a stop, confirming to the practitioner that such seating of rod 306' relative to hole 316 has in fact occurred. The length of the confirmation rod 306' will be approximately equal to 2R, positioning the distal end of rod 306' at or near the center of the disc space to be operated on (only laterally offset therefrom).

Figure 10:
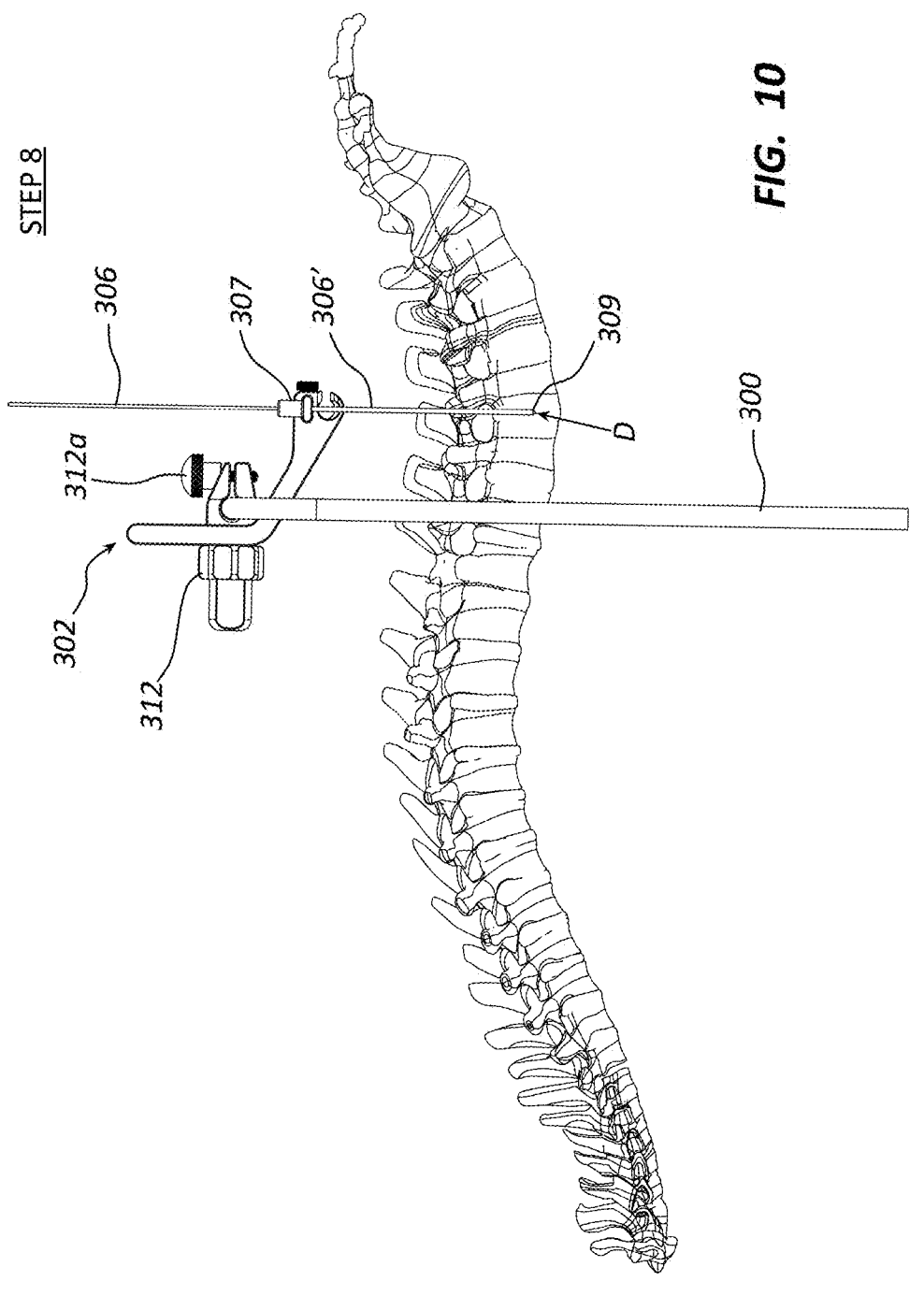
Figure 11:
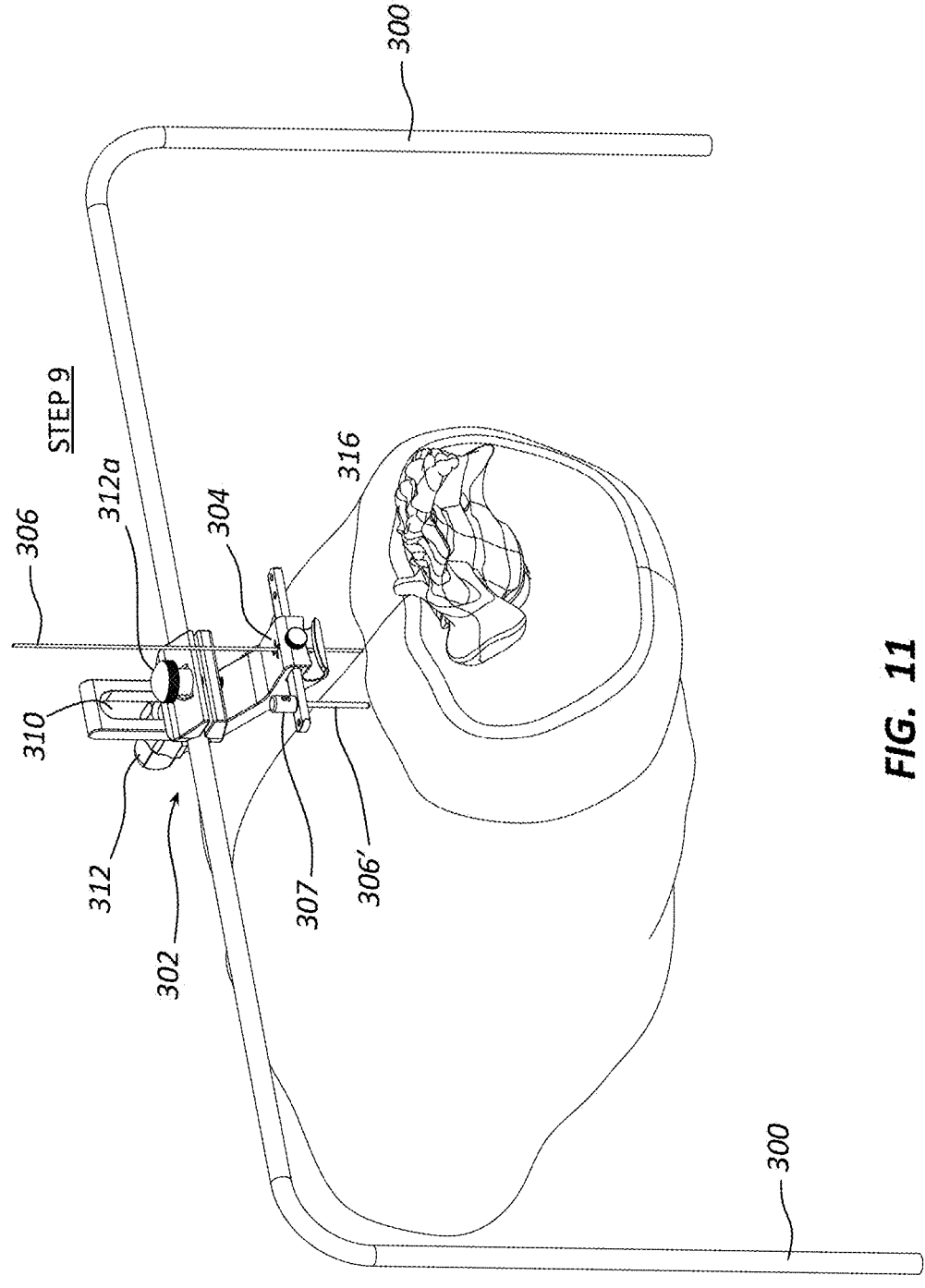
Figure 12:
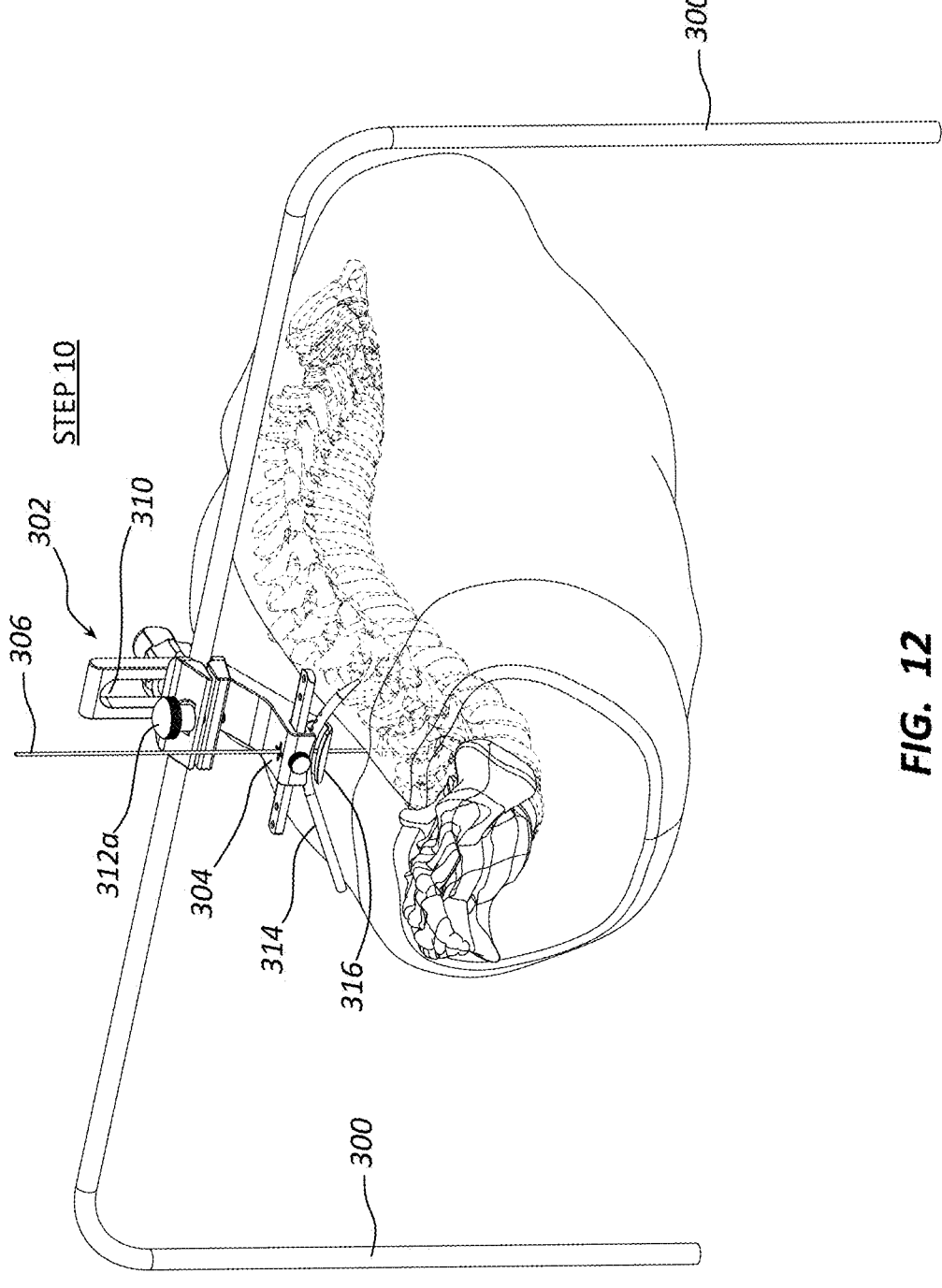

Referring to FIG. 10, additional adjustments can be made so that the tip 309 of confirmation rod 306' is at the same level as the center of the disc space "D" and at the desired angle, e.g., as seen on a lateral fluoroscopic view. Turning now to FIG. 11, after making any needed adjustments, rod insertion guide 302 is securely clamped in place by tightening the provided knobs or other structure (not shown) for securing the crossbar 300 (e.g., to the bed or operating table) and the rod insertion guide 302 to the crossbar 300 (e.g., with knob 312a). As shown in FIG. 12, curved rod 314 can be placed into rod insertion guide 302 and advanced towards the exterior skin surface of the patient. As shown, curved rod 314 may be held or guided within a correspondingly curved guide structure 316 of rod insertion guide 302. For this step, the confirmation rod 306' may have first been removed, as shown.

Use of confirmation rod 306' (and/or rod 306) is advantageous as it provides the practitioner with valuable confirmatory measurement information specific to the patient's skeletal and other geometry, so that once the curved tool 314 is advanced along the posterior to lateral pathway, it arrives at or very near the desired center of the disc targeted for fusion or other procedure being performed.

Figure 13:
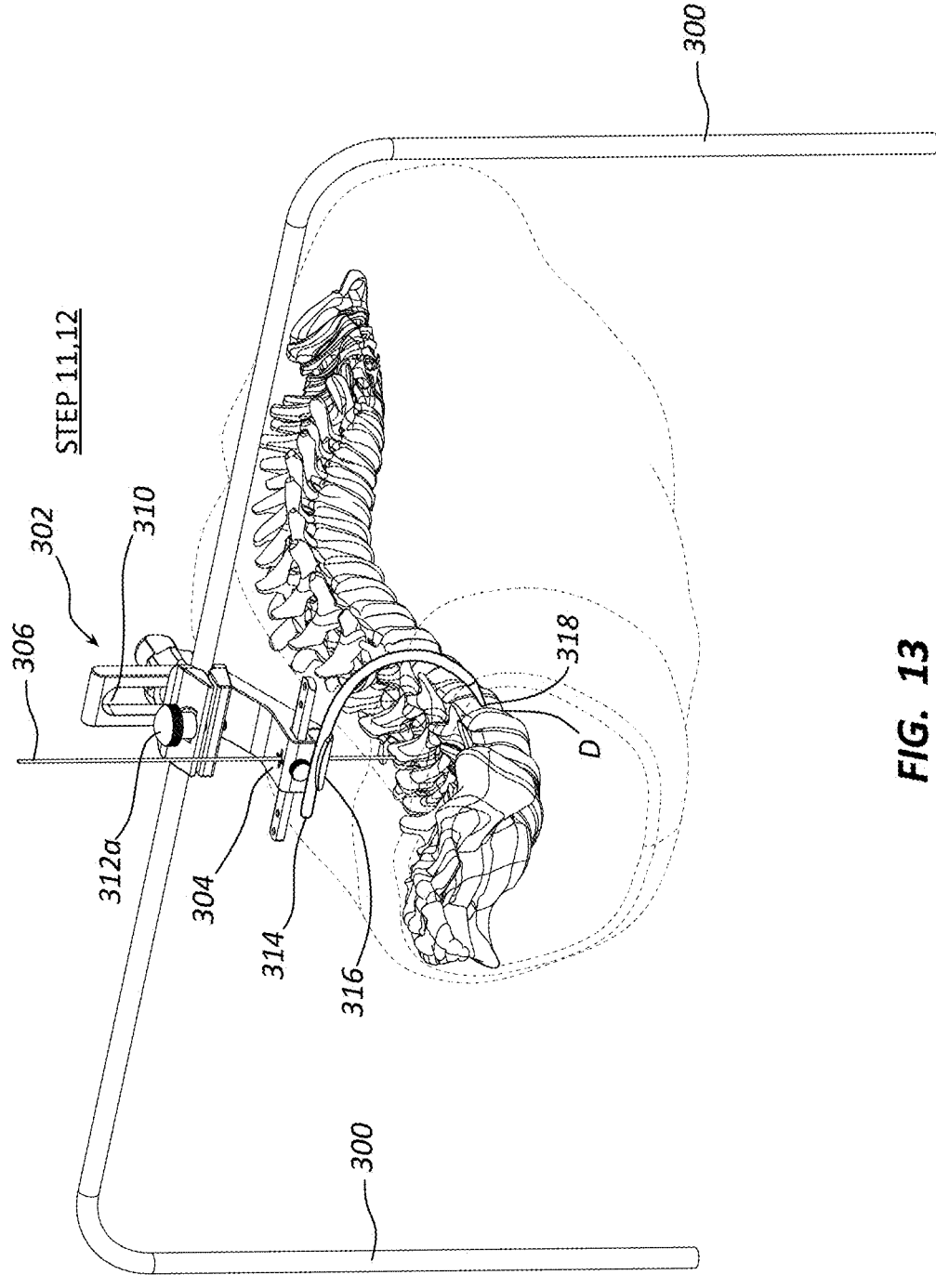
Figure 14:
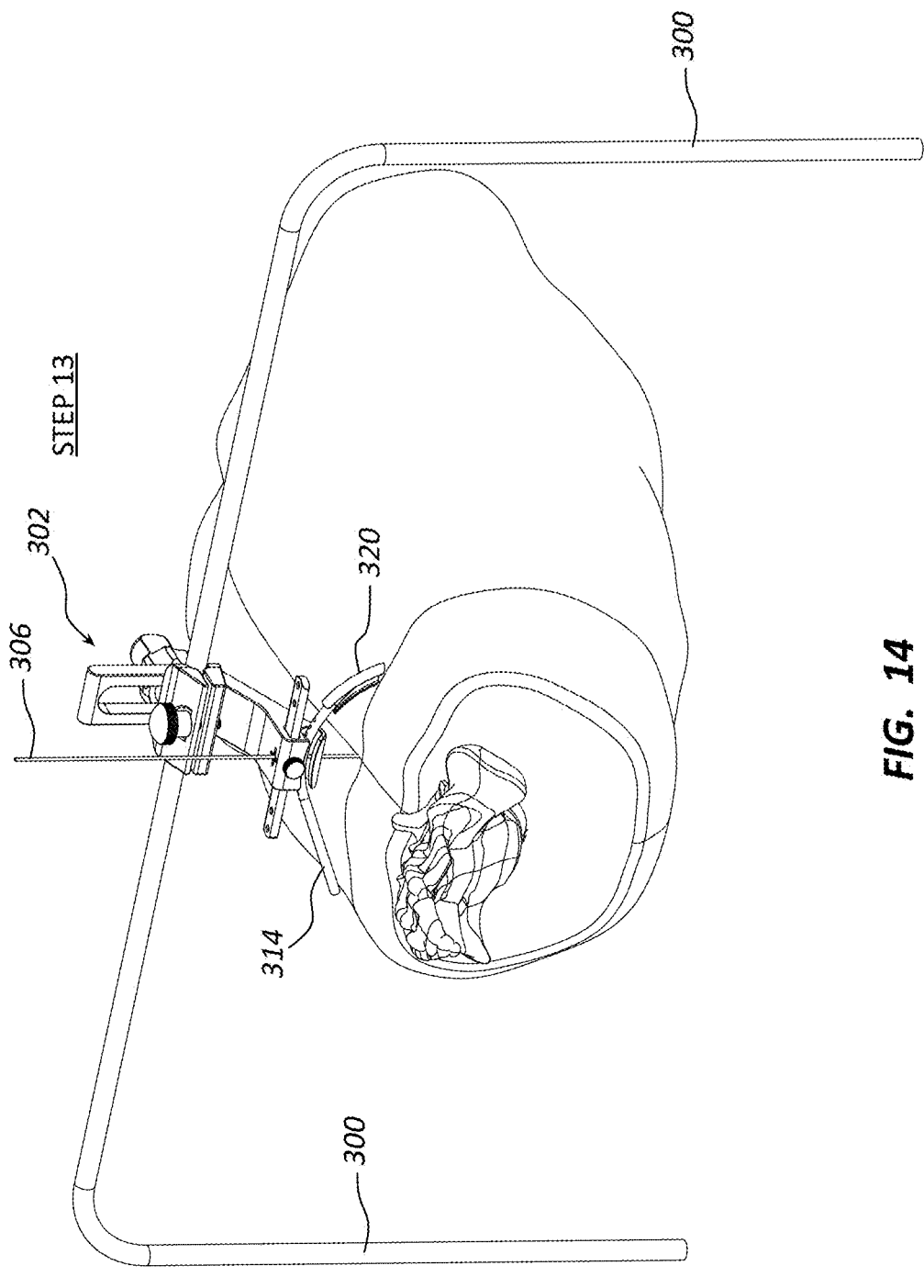
Figure 15:
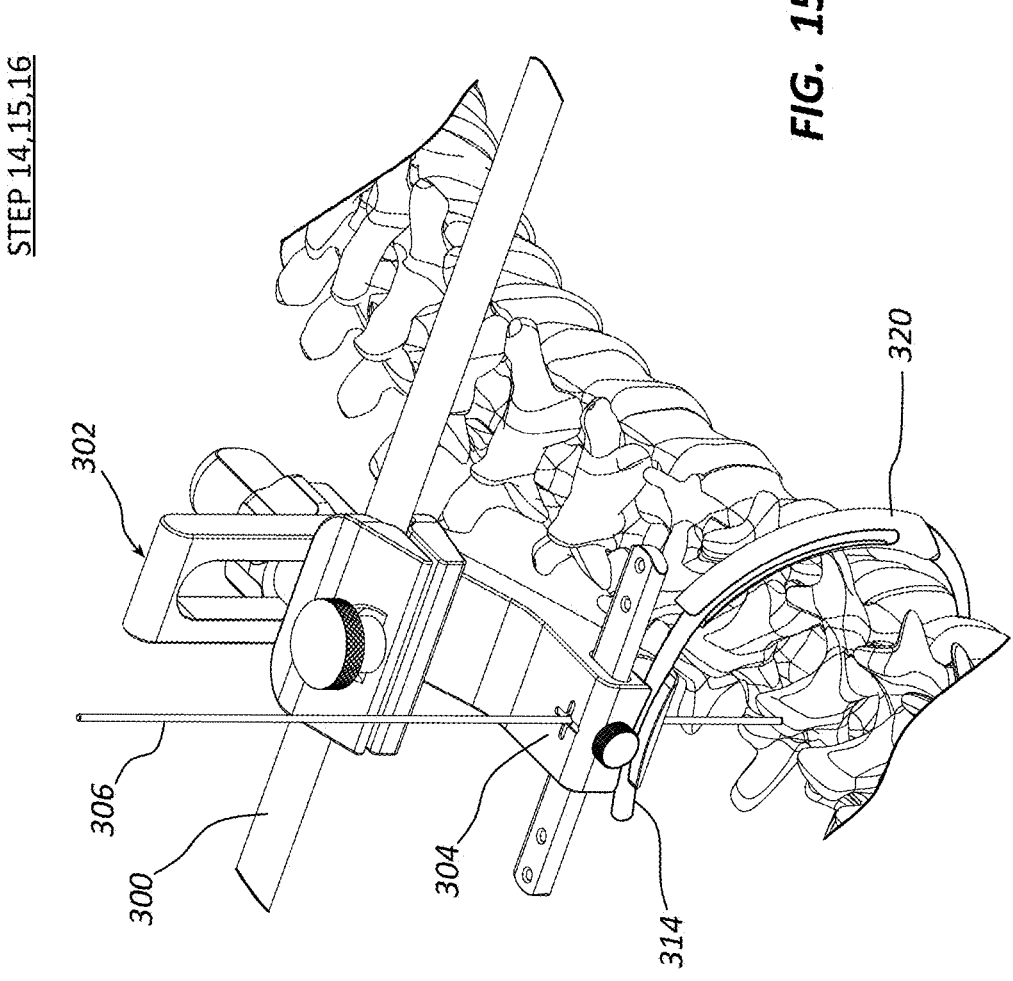

As shown in FIG. 13, the curved insertion rod 314 enters from a posterior approach, and is advanced through the skin and soft tissues (passing through the psoas muscle) until the rod reaches the lateral aspect of the disc space "D". The tip 318 of curved insertion rod 314 should contact the lateral aspect of the disc at the center of the disc, or slightly posterior to the center, relative to the disc space "D". The practitioner may electrically stimulate the curved insertion rod 314 to check for any interaction with any nearby neurological structures, e.g., as described in Applicant's other patents and applications (e.g. U.S. Pat. Nos. 8,740,956; 8,845,693; 9,668,775; 8,986,318; 9,084,633; 10,070,926; 9,486,257; 9,883,898; 10,278,737; and 10,058,361), each of which is herein incorporated by reference in its entirety. Referring to FIG. 14, if the path of the curved insertion rod 314 is correct, then rod 314 is removed and reinserted through curved cannula 320 with an outer sleeve to provide congruency.

Figure 16:
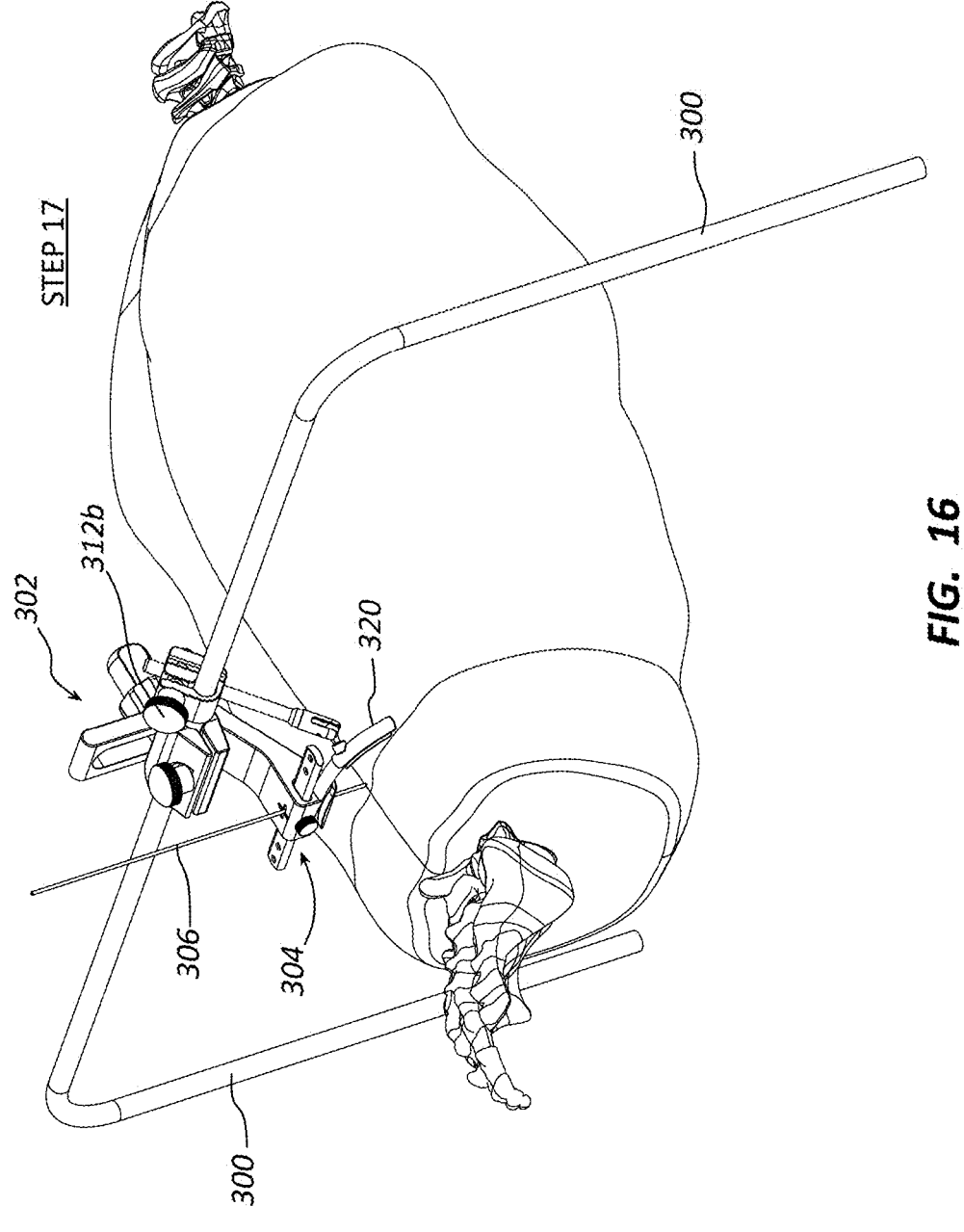
Figure 17:
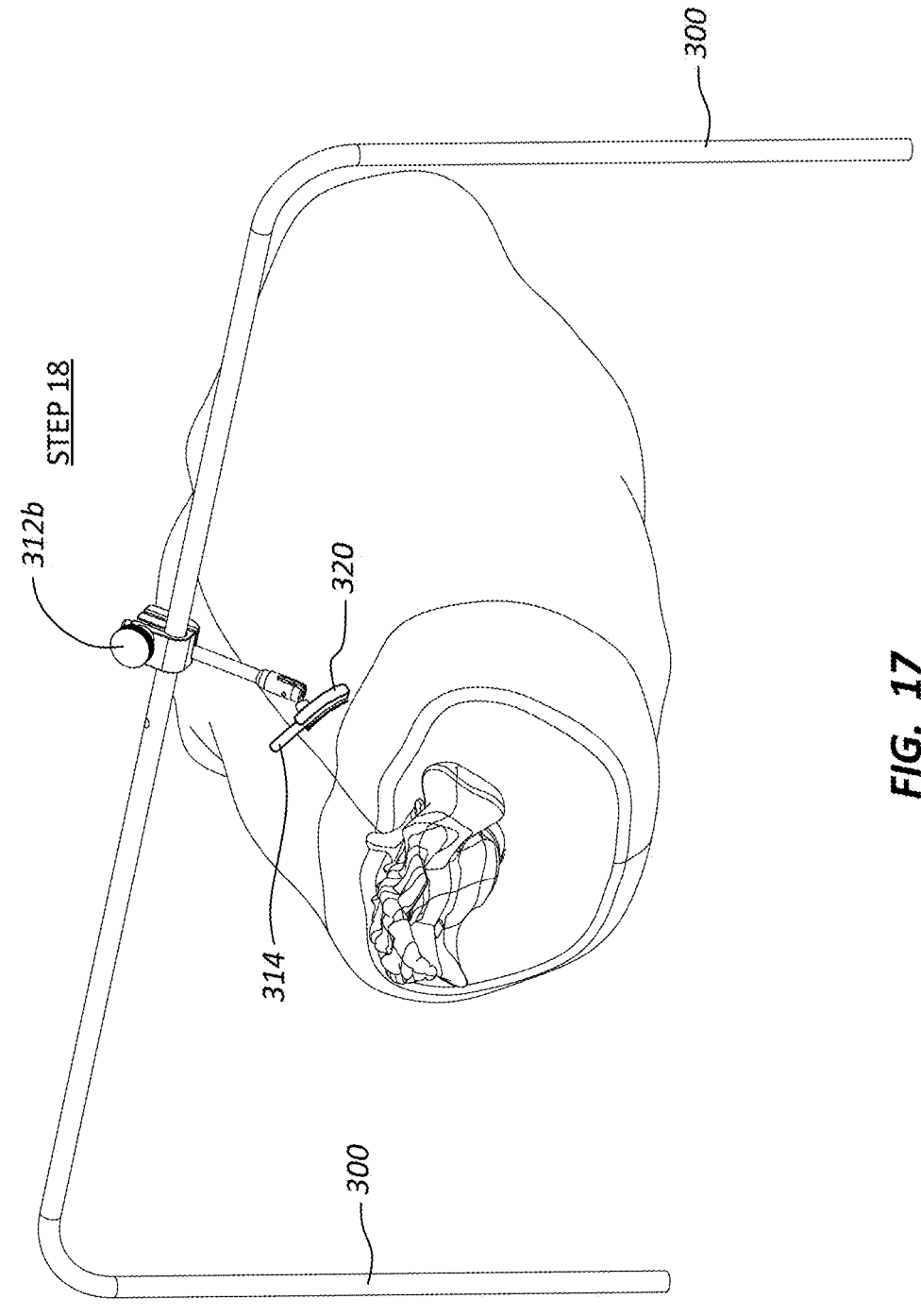
Figure 18:
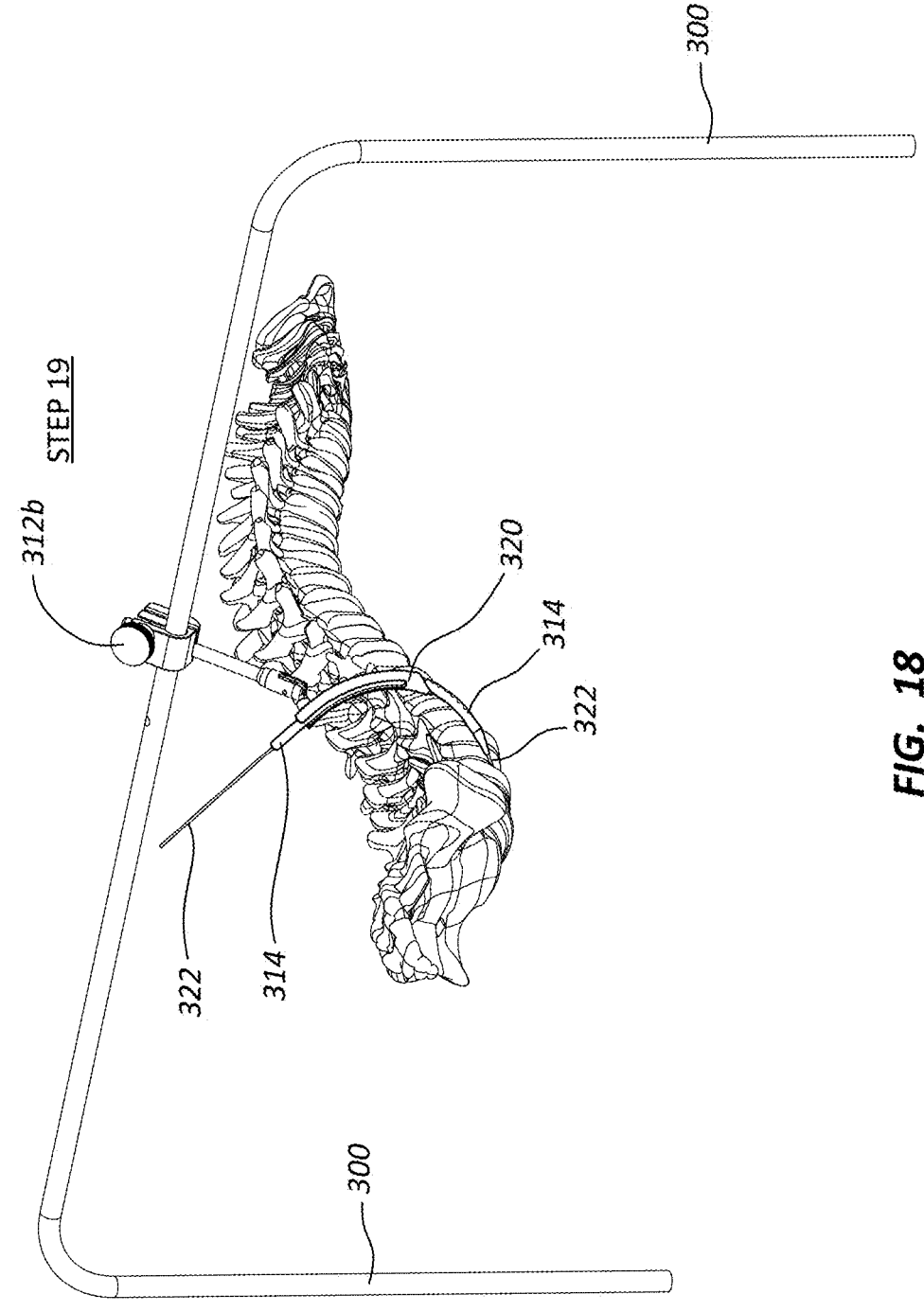
Figure 19:
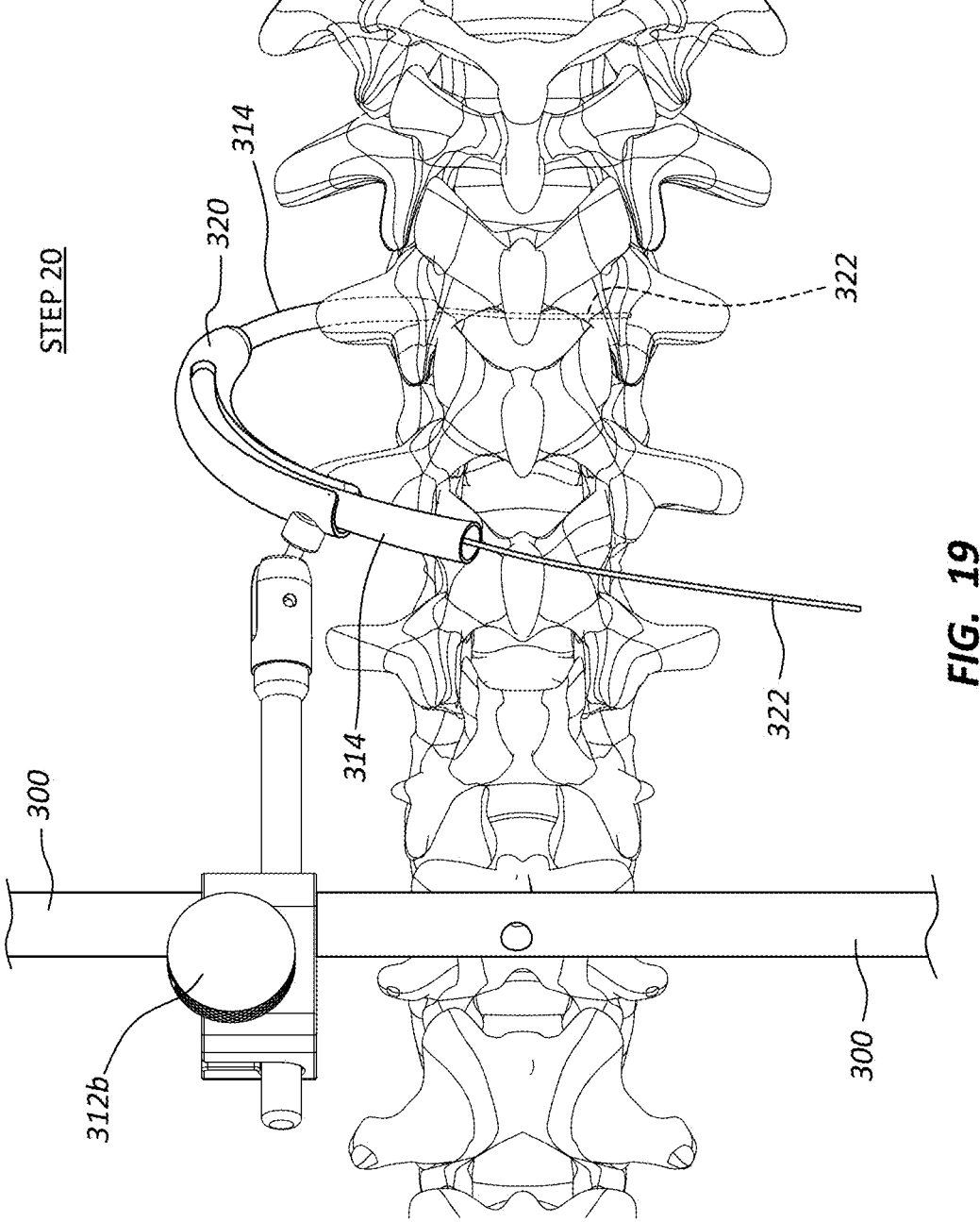

As shown in FIG. 15, the curved rod is again advanced to the lateral aspect of the disc (e.g., through cannula 320). A small incision can be made through the skin to allow for the cannula 320 to be advanced over the curved insertion rod 314. The cannula 320 with its sleeve are advanced through the soft tissue (including through the psoas muscle in the posterior to lateral approach pathway), over the curved insertion rod to the skin level. As shown in FIG. 16, the cannula 320 can be securely clamped to the crossbar 300 or other anchor point by tightening an appropriate knob (e.g., 312b) or other securing mechanism, securing the cannula 320 in place, which provides a curved posterior to lateral pathway directly to the desired disc space. It will be apparent that various mechanisms can be used for securing the cannula 320 relative to any anchoring structure (e.g., crossbar 300 or otherwise), any of which are within the scope of the present disclosure. As shown in FIG. 17, at this point, the rod insertion guide 302 may then be removed. Referring to FIG. 18, a guidewire 322 can be placed through the cannula 320 and/or curved insertion rod 314 (e.g., where rod 314 is hollow), passing along and through the disc space through to the opposite side of the disc annulus, as shown in FIG. 19. Fluoroscopy can be used to confirm correct placement of the guidewire.

Figure 20:
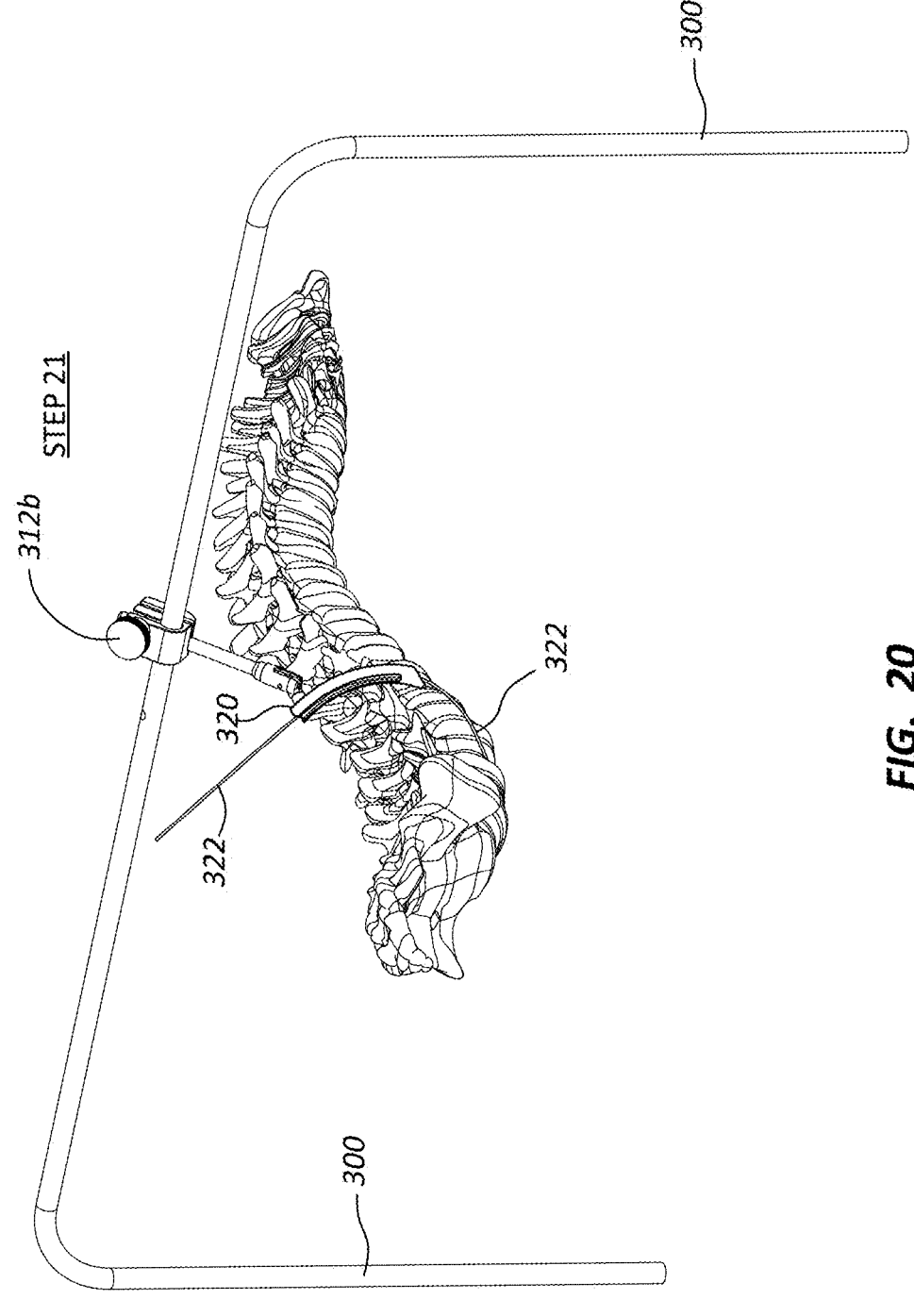

As will also be apparent from FIG. 19, in an embodiment, the guidewire 322 may be secured relative to one or both endplates of the target disc space, providing greater stability to any operations subsequently performed in the disc space (e.g., clearing). For example, by securing both ends relative to the end plates, clearing may be achieved with a subsequently placed cutting device, with anchoring provided at 2 points, at both ends of the disc space. As shown in FIG. 20, taking care not to retract the guidewire 322, the curved insertion rod 314 can be removed, leaving the guide wire 322 within the cannula 320, in position.

Figure 21:
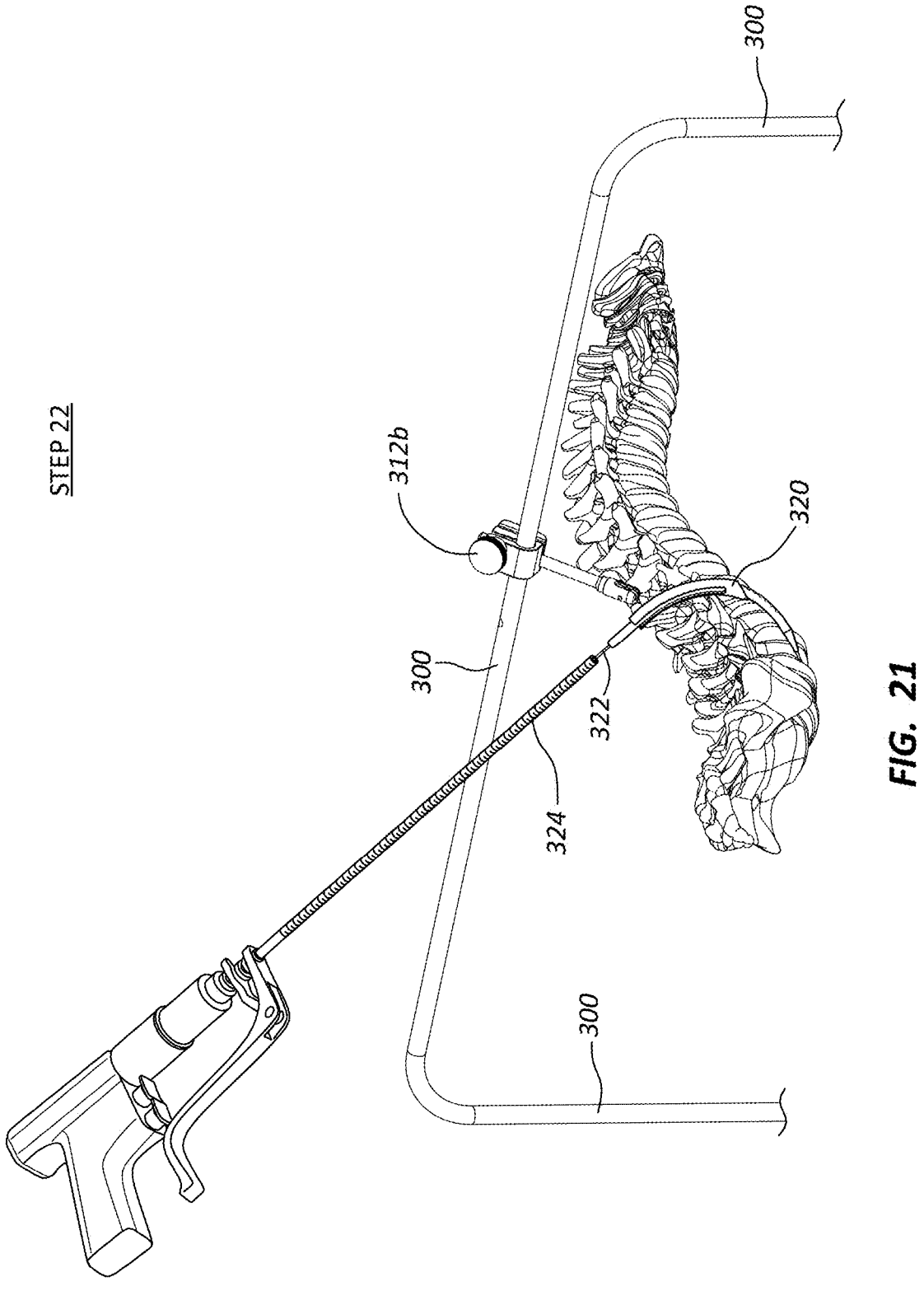
Figure 22:
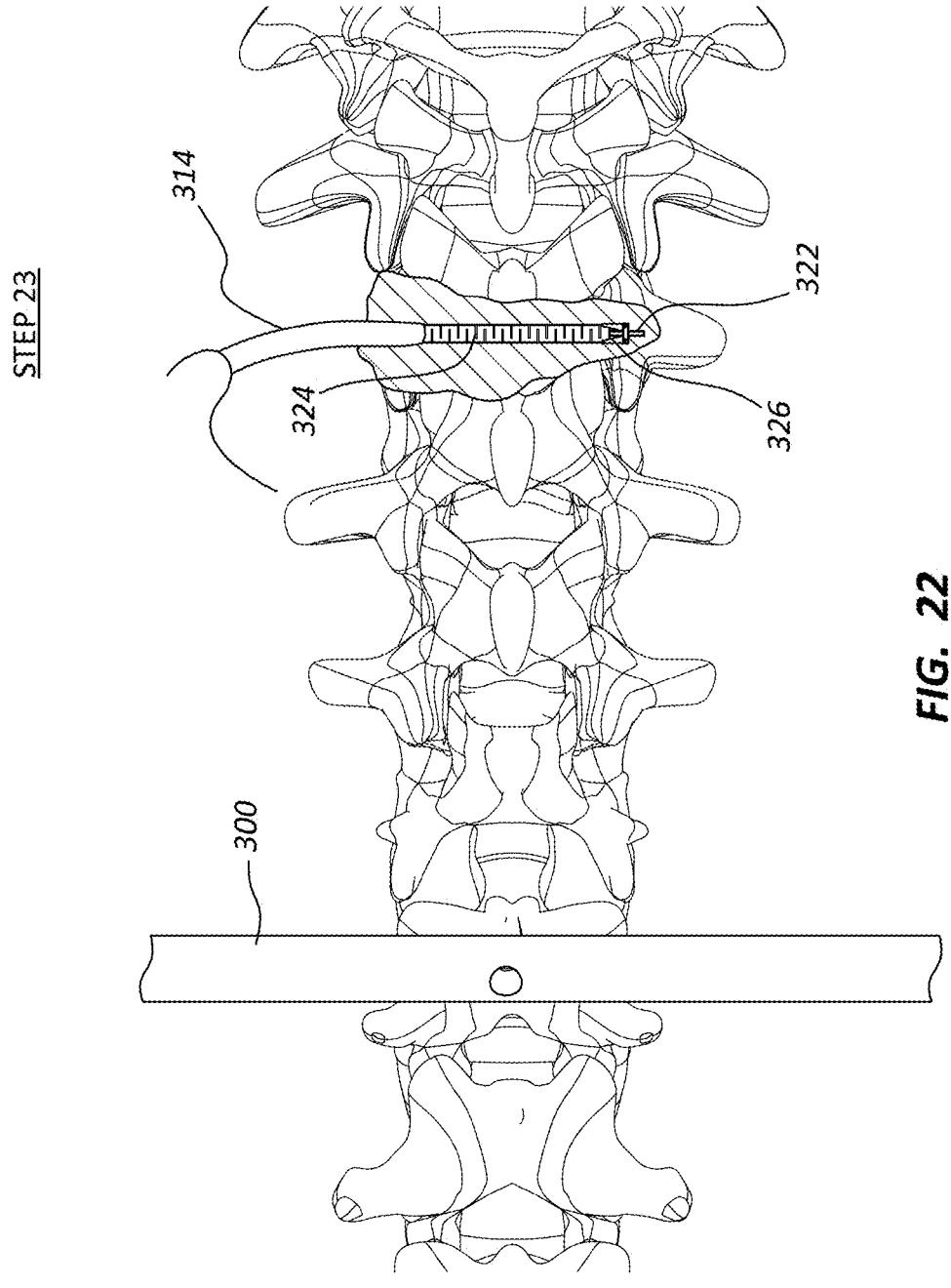
Figure 23:
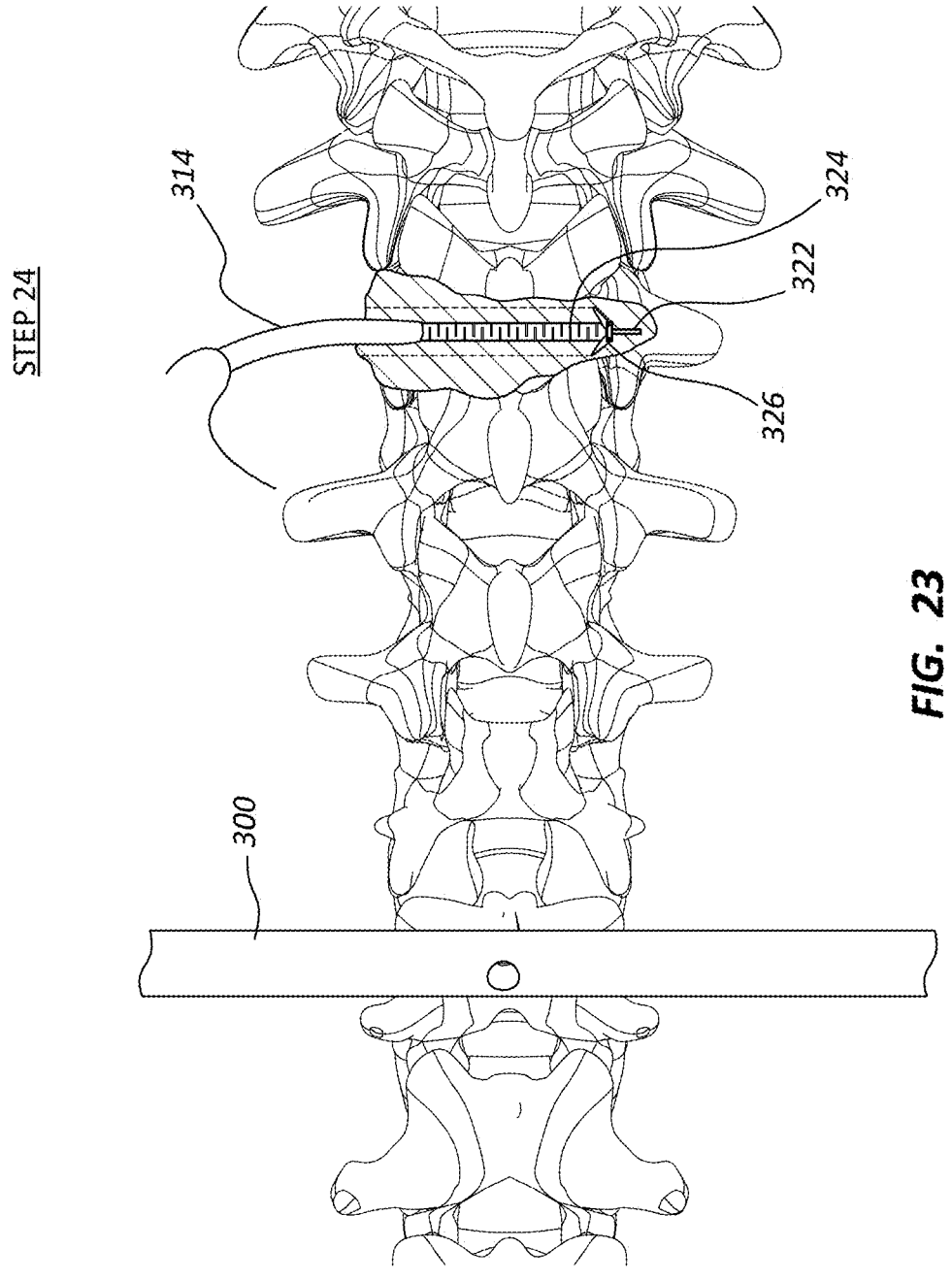

Referring to FIG. 21, a flexible cutting tool 324 (e.g., such as any described in patent application Ser. No. 16/735,374, other of Applicant's applications already referenced, or other cutting tools in the art) can be inserted over the guidewire 322 and through cannula 320. The flexible cutter 324 is advanced over the guidewire through the annulus and into the disc space "D", as shown in FIG. 22. Such advancement of the cutting tool 324 can be along the same posterior to lateral pathway already established. As shown in FIG. 23, under fluoroscopic visualization, the flexible cutter 324 can be used to cut a generally cylindrical opening through the endplates within the disc space "D". Such should be done carefully, and with a pulling rather than a pushing motion. For example, cutting may be initiated with the blades 326 of the cutter 324 retracted, with the distal end of the cutting device already fully advanced (e.g., through the annulus). The blades 326 may be expanded or deployed, as the cutter 324 is rotating, and the cutting device may then be slowly retracted. Once the blades 326 of cutter 324 are deployed and are cutting through the endplates, the cutter 324 is pulled back through the disc space until the desired space or opening has been cleared.

In an embodiment, disc preparation may be performed under direct visual observation, e.g., use of a fiber optic or similar tool with camera deployed along the posterior to lateral path, to aid in clearing of the disc space. The ability of a cutting tool to expand (e.g., retractable blades 326) is particularly beneficial, minimizing the invasiveness of the approach to the disc space.

At this point in the procedure, the practitioner may choose to use a "biologic" to assist in achieving fusion, such as an autograft, allograft, or other material delivered through a curved tube. In an embodiment, the practitioner may place an implant (such as an implant as described herein) within the emptied disc space to provide additional stability to the prepared disc space. For example, using the guidewire 322, a mechanism (e.g., tool) for inserting the implant is passed into the disc space along the same curved pathway already employed to access the disc space.

Figure 24:
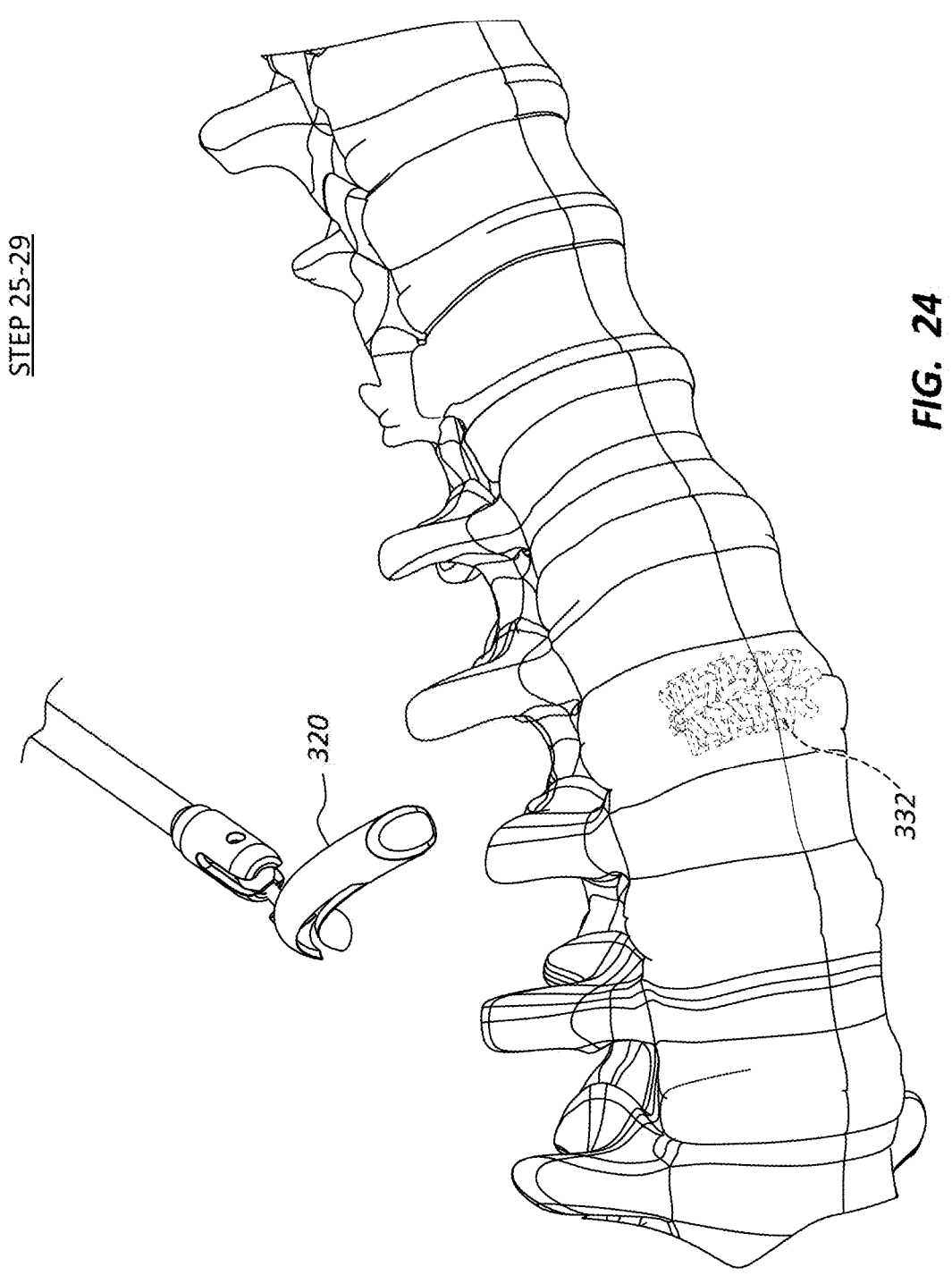
Figures 28A, 28B:
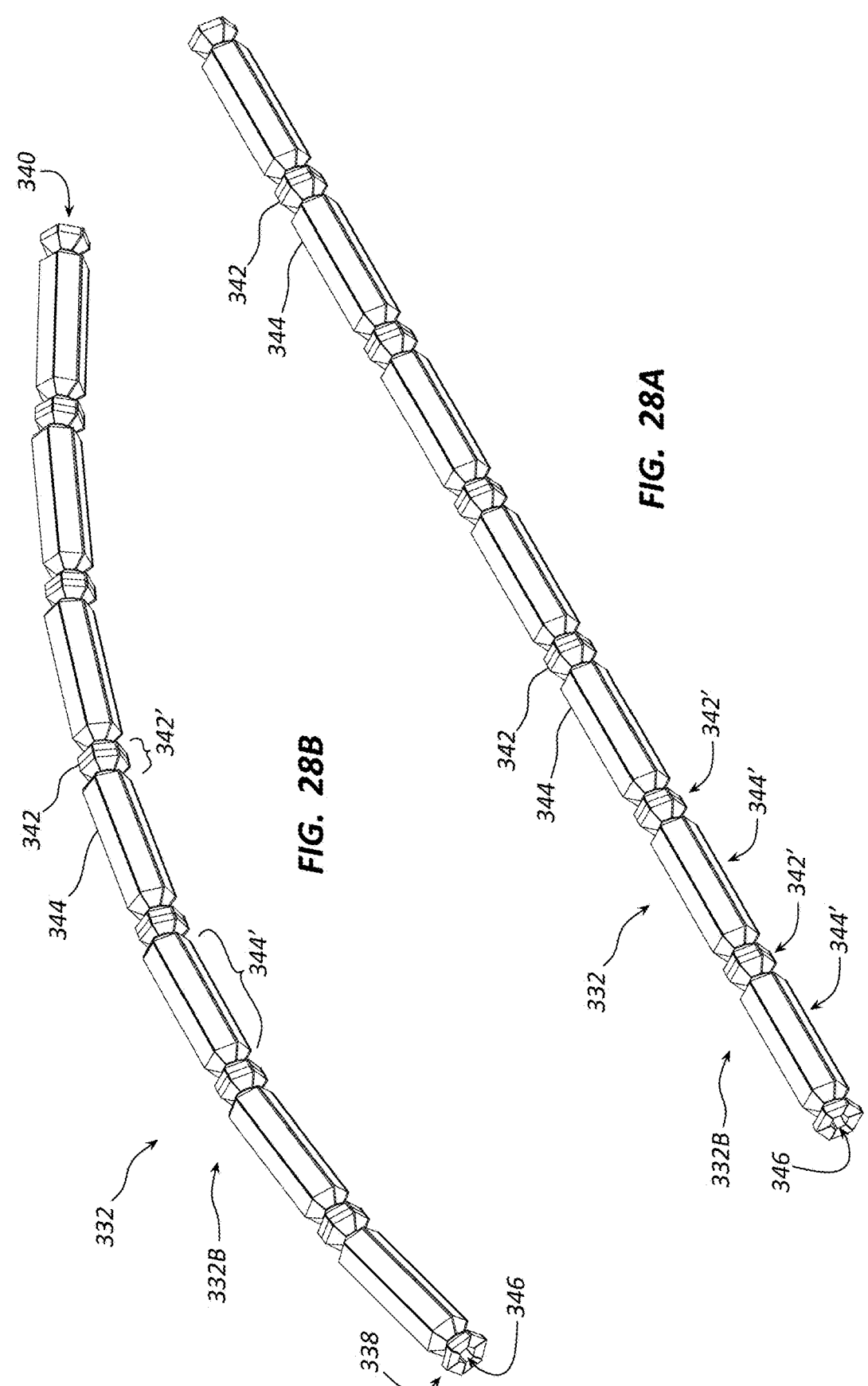
FIGS. 28A-28B illustrate the disc implant device of FIGS. 27A-27B in a rolled or folded configuration (i.e., the generally cylindrical configuration), for passage through the cannula used during a surgical procedure.

As is apparent from FIGS. 28A-28B, the implant may be passed through the tube or cannula, over guidewire 322 in the generally cylindrical, flexible configuration (i.e., resembling a series of connected sausage links) seen in FIGS. 28A-28B. Referring to FIG. 24, as each arm segment enters the cleared disc cavity, such segment can be radially expanded and axially collapsed, to provide substantial filling of the cleared disc space. As each segment of arm members is introduced into the cleared disc cavity, such segment may be radially expanded, one segment after another, until all such arm segments have been radially expanded, filling the disc space, as shown in FIG. 24. It is not necessary that the implant be formed from nitinol or another shape memory alloy, although such is possible if desired. Rather, the unique and particular structure of the implant as manufactured allows it to assume a generally cylindrical configuration (that is relatively thin, low profile, and flexible), for passage through the tube or cannula, over guidewire 322, with subsequent radial expansion and axial collapse of the arm segments of the implant, once it has reached the cleared disc space. In an embodiment, the implant device may be formed from a titanium alloy, stainless steel, or the like. In an embodiment, the material of the implant is non-resorbable, remaining in the disc space indefinitely. In an embodiment, all components of the implant may be formed from a single homogenous material (e.g., Ti-6A1-4V), rather than different components being formed from different materials. Exemplary, non-limiting materials include titanium, a titanium alloy (e.g., Ti-6A1-4V), PEEK, another suitable implantable polymer, or the like.

As described, each of the arm segments and joint segments that make up the alternating sections of arm segments and joint segments may comprise a plurality of living hinges or similar compliant mechanism structures. Each joint segment may be formed from a plurality of joint ridges, each connected to the adjacent joint ridge by a compliant hinge mechanism structure, allowing folding or rolling of the initially planar configuration seen in FIGS. 26A-27B, to the generally cylindrical configuration seen in FIGS. 28A-28C. Compliant hinge mechanism structures are also provided between the rising arm and falling arm members of each arm segment, allowing the arm segments to radially expand and axially collapse, as each pair of arm structures includes a compliant hinge mechanism structure in a middle portion (e.g., at the center) of each arm structure.

Figure 25:
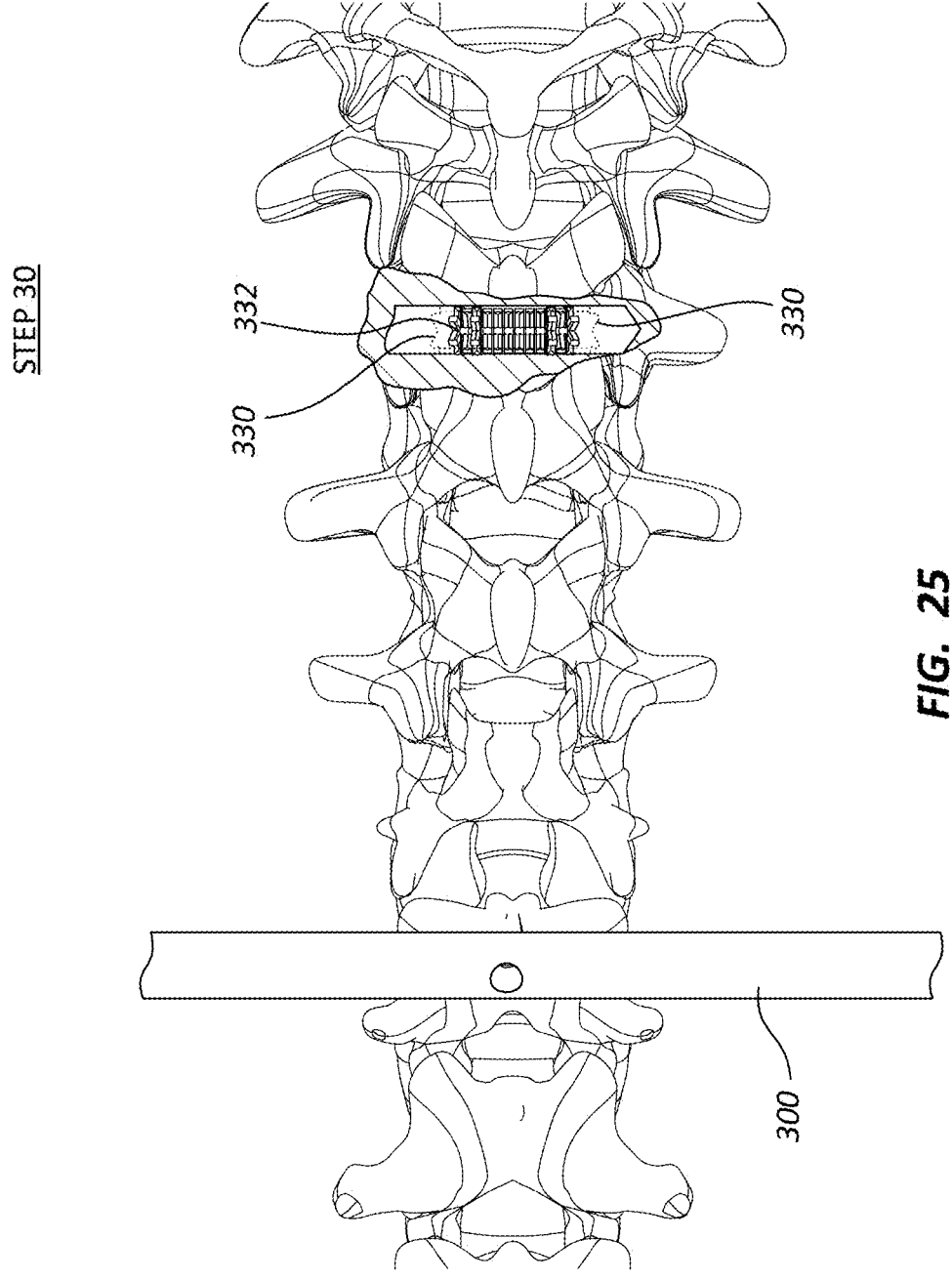

The present implants and procedures allow a relatively rigid and supportive implant structure (rigid and supportive once radially expanded in the disc space) to be inserted through the curved posterior to lateral pathway provided (in a low profile, streamlined configuration during insertion). Such may be used in combination with, or alternative to introduction of any biologic grafting material introduced into the cleared disc space. For example, once such an implant has been deployed, an appropriate biologic graft material may be employed, to facilitate the long-term success of the fusion. Finally, the guidewire 322 and cannula 320 can be removed, and the incision closed. FIG. 25 shows the radially expandable implant 332 in place, with optional grafting material 330 also positioned in the prepared disc space, e.g., around the radially extended arms of implant 332.

Figures 26A, 26B:
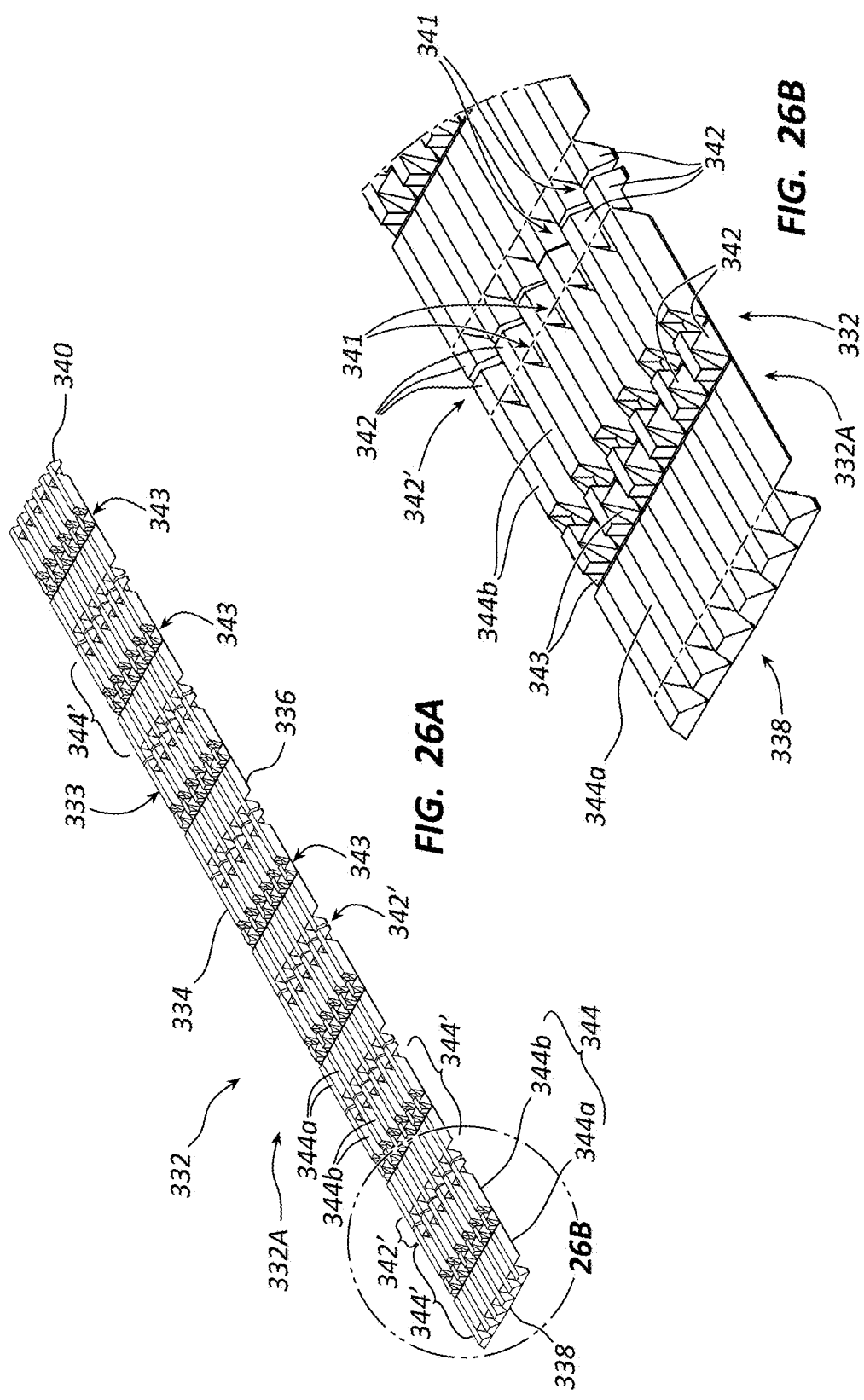
FIGS. 26A-26B illustrate an as manufactured generally planar configuration for the disc implant device, where

Attention will now be directed to FIGS. 26A-26B, which illustrate a top perspective view and a close-up view, respectively, of an exemplary implant 332 in a flat or planar configuration. For example, FIG. 26A shows a disc implant device 332 in a generally flat, planar configuration 332A (i.e., unfolded configuration) in the form of an elongated, rectangular sheet (i.e., generally horizontal, planar rectangular main body 333) with a first side 334, a second side 336 disposed opposite to the first side 334, a first end 338, and a second end 340 disposed opposite to the first end. As shown in FIG. 26B, the disc implant device 332 is shown as including a plurality of joint ridges 342 that make up the joint segment 342' and a plurality of rising and falling arm members 344a and 344b, with a compliant hinge mechanism structure 343 positioned between each respective rising and falling arm member 344a and 344b, respectively. Both arm member portions 344a and 344b, with the compliant hinge mechanism structure 343 therebetween, make up each arm member 344, while the plurality of arm members 344 in a given segment, make up the arm segment 344'. Each segment 342' of joint ridges 342 is repeated in an alternating pattern, wherein each set or segment of joint ridges 342 is adjacent to a set or segment of arm members 344, and vice versa, with sections of structures 342 and 344 alternated relative to one another, along the length of device 328. As shown, the ends 338 and 340 may each include just a portion (e.g., half) of the joint ridge segment structure 342', rather than the pair of such ridge structures 342 shown elsewhere in the device 332 . The joint ridges 342 include a living hinge, compliant mechanism structure 341 between each joint ridge structure, so as to allow the overall structure to be folded side to side (334 to 336) and collapsed to form a plurality of generally cylindrical (e.g., polygonal) joint segments (e.g., defined by a polygon having 3-12, 6 to 10, or 6 to 8 sides). By way of example, the illustrated configuration includes 6 joint ridges 342 separated by living hinge compliant mechanism structures 341, that fold together (side 334 to side 336) to form a hexagonally shaped joint between adjacent arm sections 344'. The arm members 344 are similarly configured to be folded (side 334 to side 336) to form a generally cylindrical arm structure defined by the plurality of arms (e.g., 6 arms, forming a hexagonal prism— i.e., which is a generally cylindrical structure as defined herein). Each arm 344 includes a living hinge compliant mechanism structure 343 in its middle section (between rising arm member 344a and falling arm member 344b), allowing each arm member 344 to radially expand and axially collapse, as the mid-portion 343 of such arms are radially expanded outward, bringing adjacent joint segments 342' defined by the joint ridges 342 towards one another, as the structure radially expands and axially collapses. It will be appreciated that the compliant hinge mechanism structure 341 between joint ridges extends latitudinally, along a portion of the width of device 328 (e.g., parallel with a latitudinal axis parallel to an axis connecting sides 334 and 336), while the compliant hinge mechanism structure 343 between arm members 344a and 344b extends longitudinally, along a portion of the length of device 328 (parallel with a longitudinal axis parallel to an axis connecting ends 338 and 340). This allows the compliant hinge mechanisms associated with joint ridges 342 to allow the joint segment to fold or roll about the longitudinal axis of the device 328, while the compliant mechanisms associated with arm members 344 allow the arms (and arm segments made up of 6 or another number of such arms) to radially expand and axially collapse the arm segment 344'.

Figures 27A, 27B:
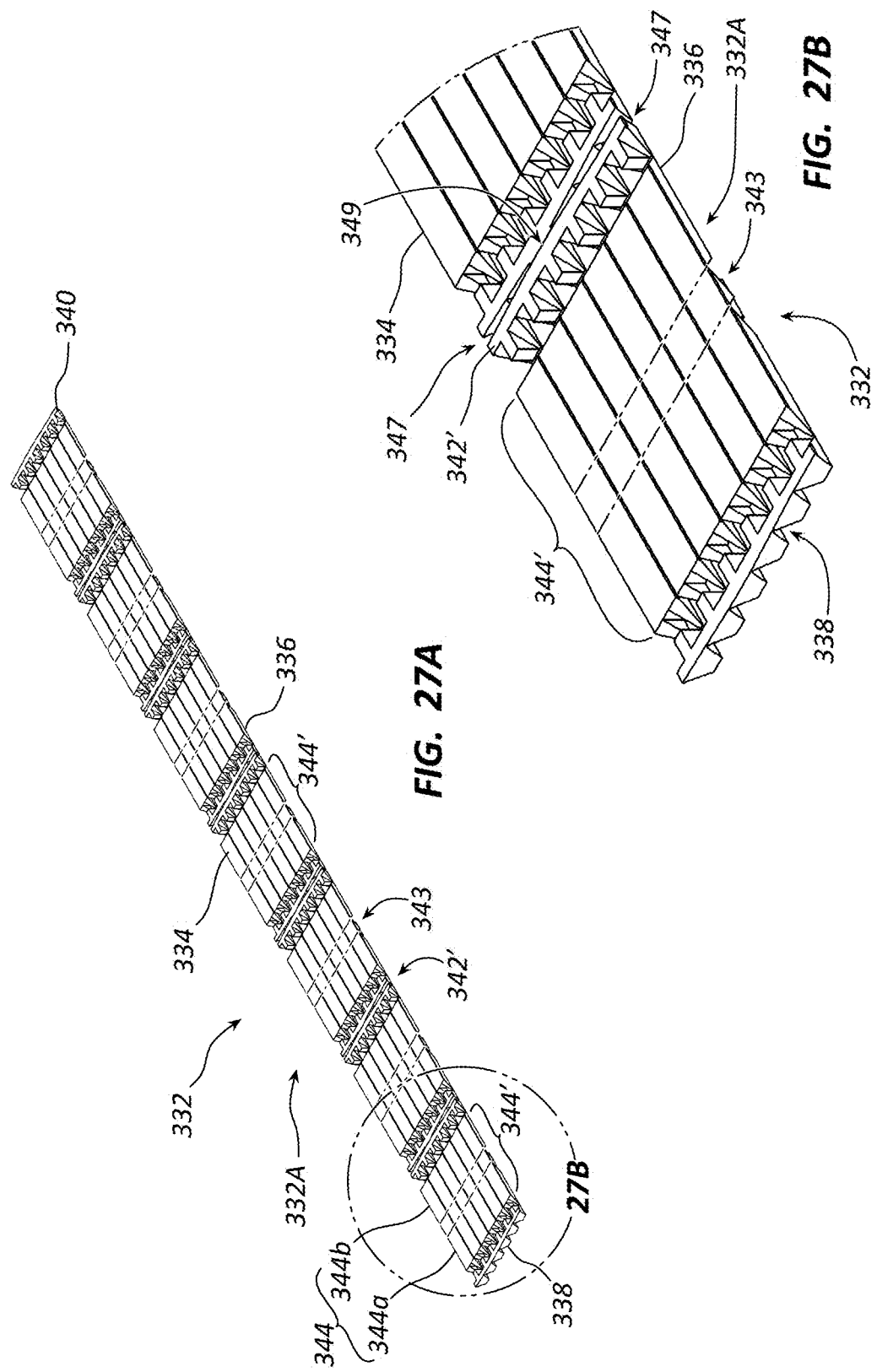
FIGS. 27A-27B illustrate an as manufactured generally planar configuration for the disc implant device of FIGS. 26A-26B, flipped over.

FIGS. 27A-27B illustrate a bottom perspective view and close-up view, respectively, of the same exemplary implant 332, still in the same flat configuration 332A as shown in FIGS. 26A-26B. As shown, a split 347 is provided between the two halves (e.g., right and left halves) of joint ridges 342 that make up the joint segment 342'. This split is not complete however, with a middle portion (at 349) of such joint segment halves being attached to one another. The connected portion 349 connects one arm segment to the next (through the right and left halves of the joint segment 342'), while the incomplete split 347 otherwise separating the two halves of the joint segment 342' provides flexibility to the overall structure, allowing one arm segment to be flexed or bent, relative to the next adjacent arm segment, allowing the overall structure to assume a curved configuration, as shown in FIGS. 28A-28B. While the joint connecting the segment does allow for curvature/flexibility, it is also employed as a convenience. Similar characteristics could be provided without such a linkage, if the assemblages (arm segments) were placed in individually. The linkage conveniently allows manufacture in one piece without assembly.

In some embodiments, the disc implant device can be manufactured in a planar, flat configuration, but which is configured to be rolled and/or folded into a generally cylindrical shape (using compliant hinge mechanisms 341), generally forming a cylindrical structure (e.g., a polygonal prism, such as a hexagonal or octagonal prism, which approximates a cylinder), or a series of such cylindrical structures, linked together, similar to a series of sausage links. As shown in FIGS. 28A-28B, such a generally cylindrical shape can include a hollow center and a generally circular opening (e.g., an octagonal or hexagonal opening 346 shown) at the first end 338 and at the second end 340. Such an opening can be sized to accommodate a guidewire 322. FIG. 28A illustrates a perspective view of the implant in a folded, but straight configuration. For example, FIG. 28A shows disc implant device 332 in a generally cylindrical configuration 332B, where device 332 has been folded (i.e., rolled) such that a first side 334 of the disc implant device 332 is adjacent to a second side 336 of the disc implant device 332. Disc implant device 332 is shown with a plurality of joint segments 342' in a folded configuration and a plurality of arm segments 344', also in a similar polygonal, generally cylindrical folded configuration. While not illustrated, a sleeve could be provided, fitted over each joint segment 342', if desired (e.g., to provide a substantially smooth flush surface, from one arm segment 344' to the next). FIG. 28B illustrates the same implant device 332 in a folded configuration 332B, but showing how such a structure is flexible due to the partially split structure 347/349, so as to be capable of assuming a curved configuration. Such characteristics allow for the device 332 in the generally cylindrical configuration 332B to pass through a cannula or tube, e.g., over a guidewire 322, where such device is sufficiently flexible to bend as it is delivered to the disc location. For example, FIG. 28B shows disc implant device 332 in the generally cylindrical configuration 332B, where the device 332 has been folded (i.e., rolled) such that a first side 334 of the disc implant device is flush or adjacent with a second side 336 of the disc implant device 332. The plurality of joint segments 342' defines a curvature of the device from the first end 338 to the second end 340. It should be appreciated that the device 332 in this configuration 332B is flexible, so that the curvature of the disc implant device 332 is configurable according to any number of desired curvatures, e.g., ranging from straight (180 degrees) to forming a full semi-circle, or perhaps even more tightly curved, as needed. The illustrated device is shown as including 7 arm segments 344' defined by arm members 344, with 6 joint segments 342' defined by joint ridges 342 positioned between adjacent sections of arm segments 344'. The spacing, length, and total number of such alternating sections may vary, as desired (e.g., determined by patient size).

Figure 28C:
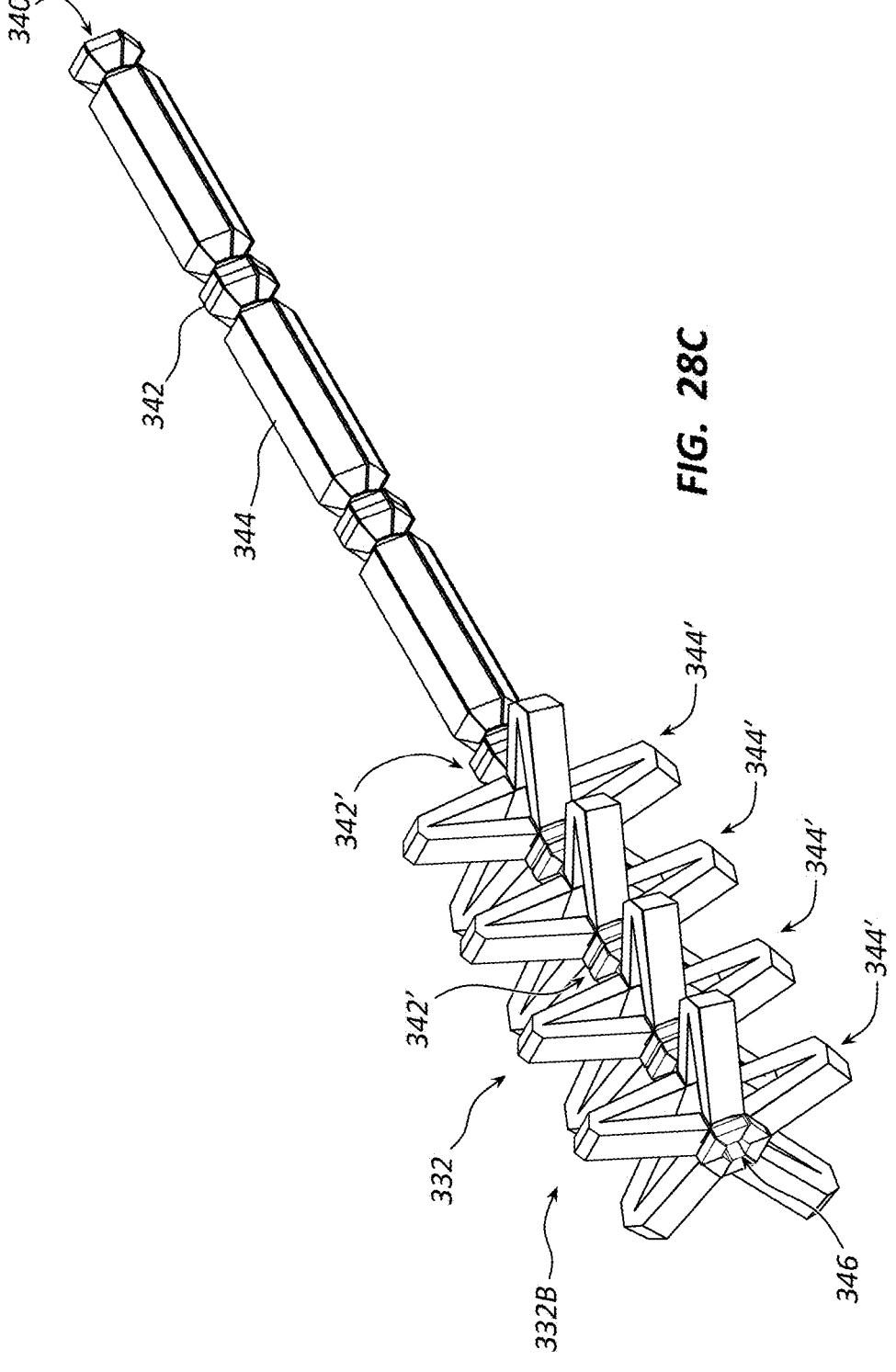
FIG. 28C illustrates the disc implant device of FIGS. 28A-28B, showing some of the arm segments having been axially collapsed, and radially expanded, for filling the space within the disc during the surgical procedure.

FIG. 28C shows a configuration similar to that shown in FIGS. 28A-28B, but in which the leading arm segment 344' has been axially collapsed and radially expanded. Each of the following arm segments is similarly capable of such axial collapse and radial expansion. Turning to FIGS. 29A-28B, these Figures show how the implant device may appear once all arm segments 344' have been radially expanded.

FIG. 29A illustrates a perspective view of the implant device 332, showing a configuration 332C that results upon axial collapse and radial expansion of arm segments 344'. For example, disc implant device 332 is shown in the radially expanded, axially collapsed configuration 332C (e.g., axially collapsed and radially expanded from the folded configuration 332B shown in FIG. 28B), such that the first end 338 of the disc implant device 332 is axially compressed toward the second end 340 of the disc implant device 332. The corresponding ends of each arm segment are brought together, pushing the rising and falling arm members 344a and 344b radially outward, to achieve such. Each arm segment may be radially expanded independently of any other arm segment, although more typically, the arm segments 344' may be radially expanded and axially collapsed in sequence, from one end towards the other, using any suitable mechanism (e.g., one or more stops secured to the guidewire 322, so that as force is applied to one end of the implant, each arm segment axially collapses and radially expands. It will be appreciated that such a stop on the guidewire is merely one exemplary actuation mechanism, and a variety of others will be apparent to those of skill in the art, all of which are within the scope of the present invention. In this manner, each segment of joint ridges 342 form a spacing joint segment 342' between adjacent arm segments 344', where each arm segment includes a plurality of radially extending arm members 344, each arm member 344 including a rising arm member 344a, a falling arm member 344b, and a compliant hinge mechanism 343 positioned therebetween. Each set of radial arms associated with a given arm segment 344' is made up of a plurality (e.g., 6 or 8) of arm members 344, which are folded over themselves (e.g., in half), to extend radially outward. For example, the illustrated configuration includes 6 radial arms members 344 per set 344', with each arm member 344 folded over itself (e.g., 344a over 344b), to define a radial extension that is approximately half the length of each arm 344.

Each set of radial arms comprises one or more radial arms 344, which extend outward from a longitudinal axis of the disc implant device 332 and fan out. Each radial arm is disposed at a predetermined angle away from the adjacent radial arm(s), e.g., depending on the number of arm members included in each section. By way of example, the illustrated embodiment includes 6 arms, each arm being 60 degrees apart from one another (i.e., 360 degrees divided by 6). The spacing joint segments 342' and the radial arm segments 344' alternate along the length of device 332, such that a spacing joint segment is disposed between two adjacent sets of radial arm segments 344'.

As shown, angled structures may be provided on the ends of each rising and falling arm member 344a, 344b, as well as a pyramidal shaped structure associated with compliant hinge mechanism 343, which angled structures mate or interface with one another, as shown. For example, as perhaps best seen in FIG. 29A, a 45 degree angled surface may be provided on both ends of rising and falling arms 344a, 344b, where such arm members connect to one another, through the compliant hinge mechanism 343. The compliant hinge mechanism is also shown as including a pyramidal structure, which includes angled sides, so that the angled side of the rising arm 344a interfaces with the angled face of the pyramid of the compliant mechanism 343, and an opposite angled face of the pyramid of the compliant mechanism 343 interfaces with the correspondingly angled face of the falling arm 344b. Such angled faces are labeled "A" in FIG. 29A. In an embodiment, all such angled faces may be at approximately 45 degrees.

Figure 29B:
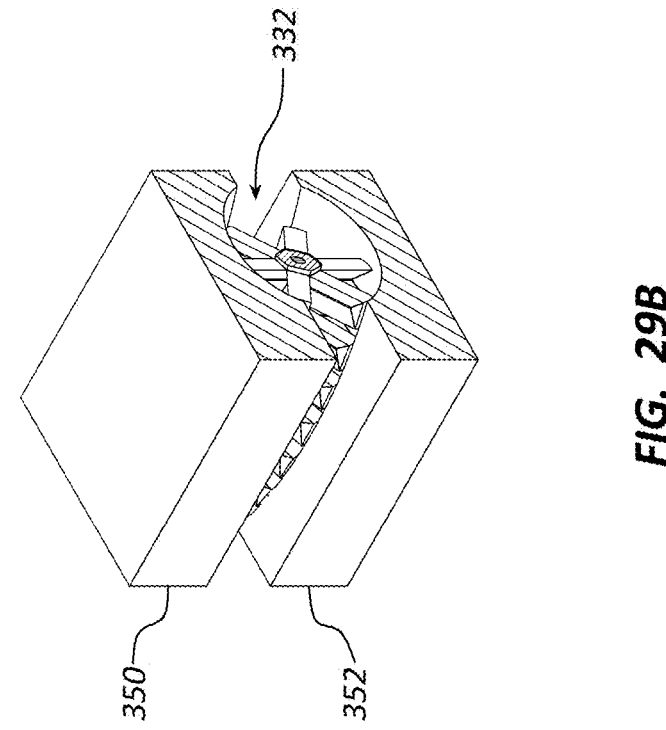
FIGS. 29A-29B schematically illustrate an exemplary disc implant device disposed within a reamed space of a spinal disc being filled.
Figure 29A:
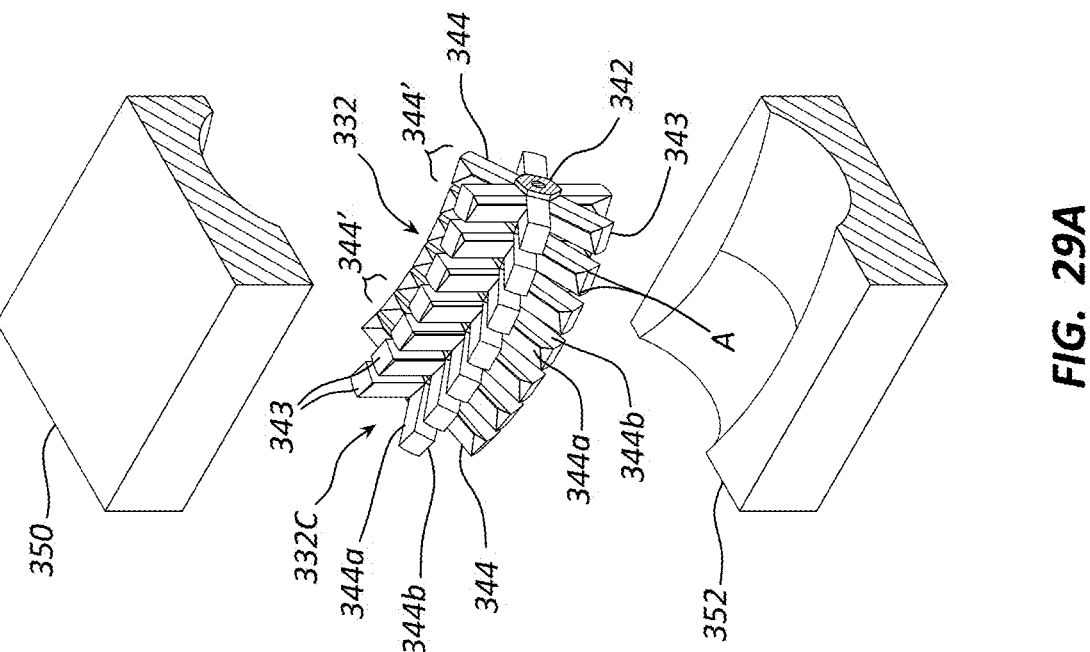
Figures 31A, 31B:
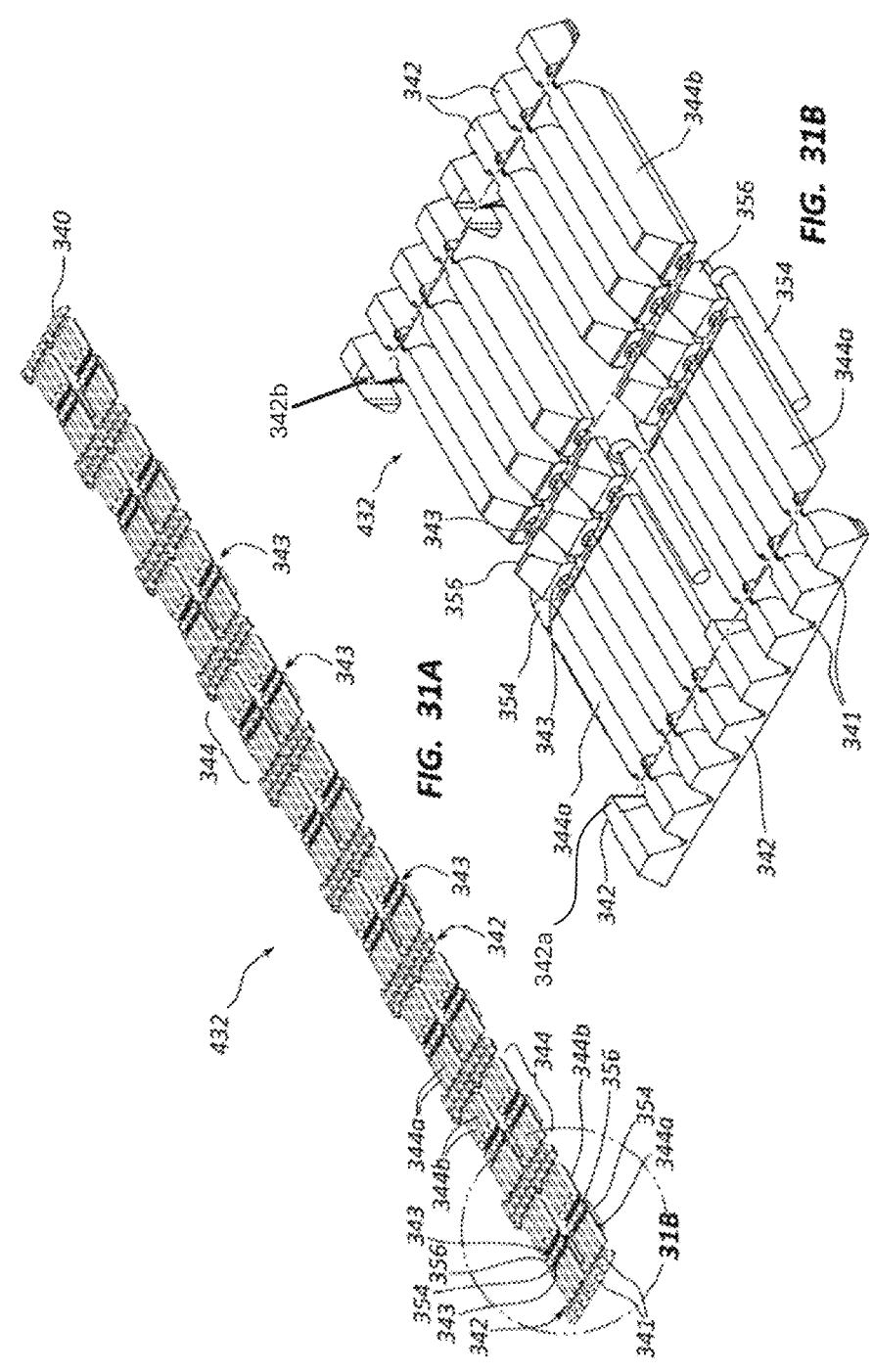
FIGS. 31A-31F illustrate another exemplary disc implant device including additional wires in tension to stabilize the implant.
Figures 31C, 31D:
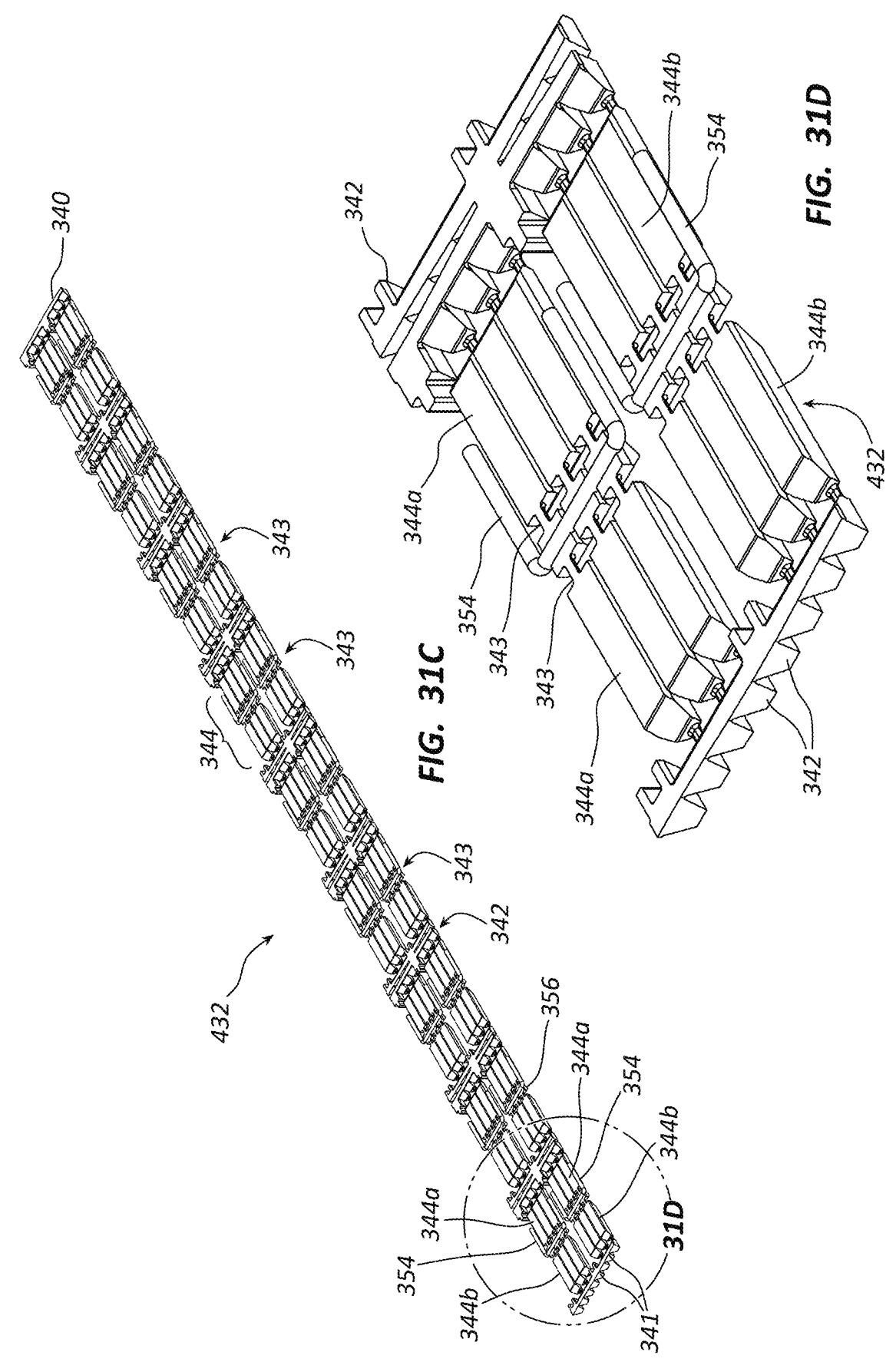
Figure 31F:
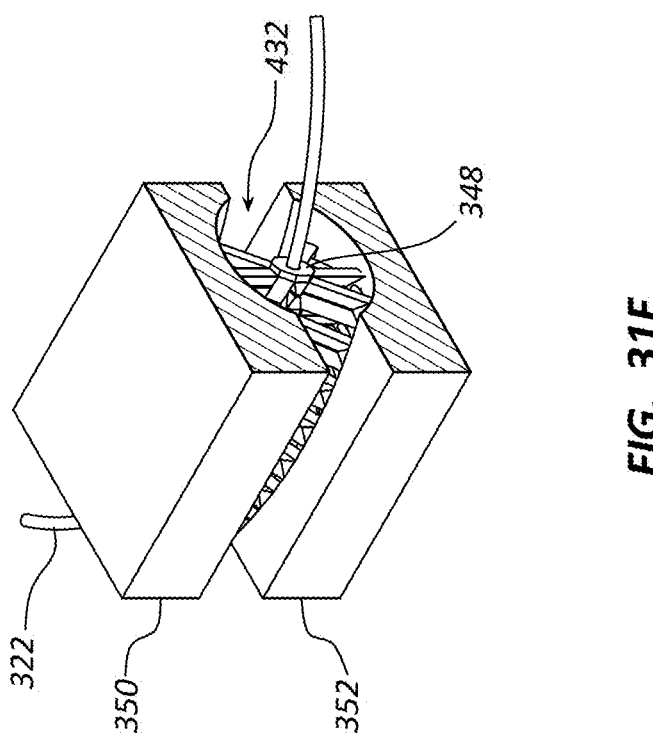
Figure 31E:
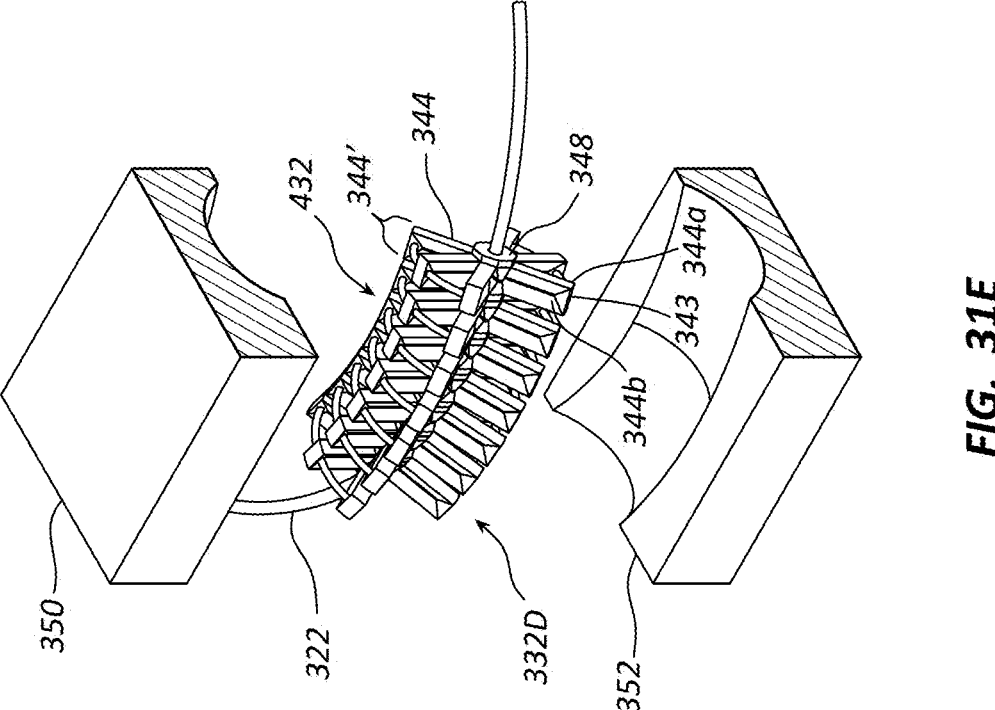

In some embodiments, as shown in FIGS. 29A-29B, each set of radial arms 344' may be in a uniform radial pattern, such that each arm 344 in a set or segment 344' is disposed equidistant from each other. Additionally, or alternatively, one or more sets of radial arms may comprise radial arms that are radially spaced apart according to different angles. FIGS. 31E-31F show such an example. Furthermore, in some embodiments, as shown in FIGS. 29A-29B, the plurality of radial arm segments 344' are shown in a uniform pattern, such that each adjacent set 344' of radial arms is disposed in the same orientation as the adjacent set or segment of radial arms 344'.

FIGS. 29A-29B also illustrate a perspective view of a curved implant with uniform arms in the axially collapsed, radially expanded configuration, schematically illustrated as disposed within a cleared disc space. For example, a schematic disc vertebrae is shown in two pieces (e.g., top disc portion 350 and bottom disc portion 352). FIG. 29A shows an exploded perspective view of the disc vertebrae portions, and FIG. 29B shows a compact perspective view of the disc vertebrae portions. The top disc portion 350 and bottom disc portion 352 are shown having an emptied out or hollow space formed in the center, between end plates of the disc, such that there is an empty cavity in which the disc implant device 332 is able to sit. The disc implant device 332 provides supports from inside the disc such that the disc does not compress or collapse and is able to support the portion of the patient's spine that corresponds to that particular disc, during and subsequent to full healing.

Figure 30A:
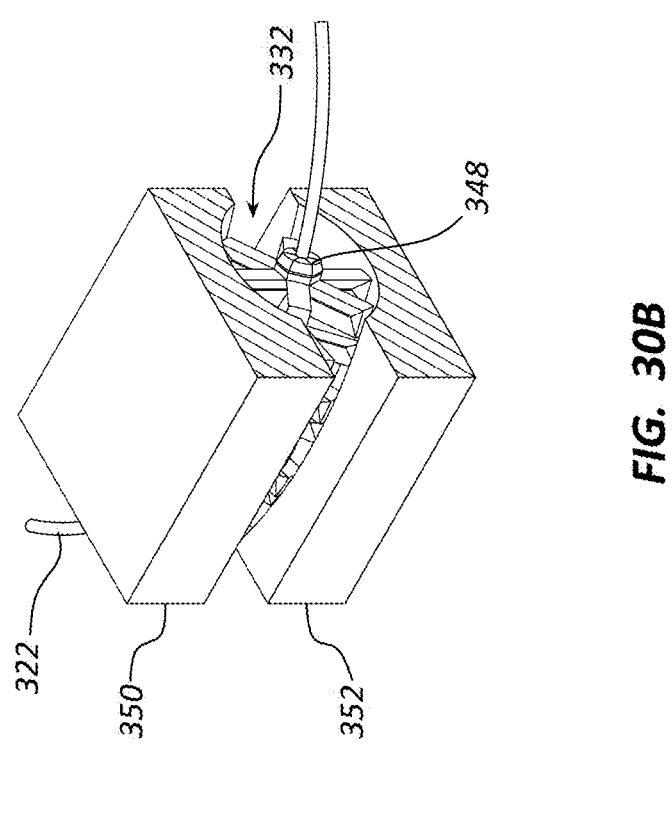
FIGS. 30A-30B illustrate the exemplary disc implant device of FIGS. 29A-29B, the disc implant device being shown threaded over a guidewire.
Figure 30B:
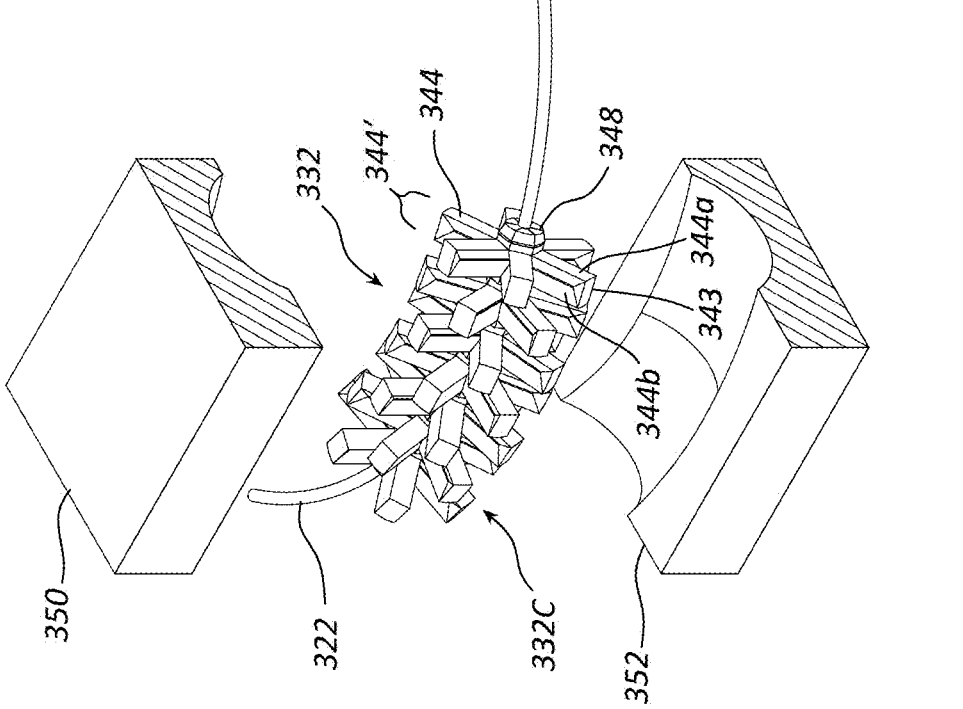

Attention will now be directed to FIGS. 30A-30B, which illustrates a perspective view of the implant 332 in the axially collapsed, radially expanded configuration. FIGS. 30A-30B show disc implant device 332 removably secured to a guide wire 322, with a stop or nut 348 which can be used to collapse the disc implant device 332 alone wire 322, once it is positioned in the cleared disc space. The curvature of the disc implant device 332 as it advances over the guidewire 322 is configured to match the curvature of the guide wire as dictated by the delivery pathway, for optimal movement of the disc implant device (in the generally cylindrical configuration as represented by FIGS. 28A-28B) towards the cleared disc space. Once the cleared disc space is actually reached, each section or segment 344' of arms 344 may be axially collapsed and radially expanded, one segment at a time, as that segment enters the disc space. Collapse and radial expansion may be accomplished by any suitable technique, e.g., by providing stops such as 348 on guidewire 322, on both ends of implant 332, to collapse implant 332 as one stop is advanced towards the other. Other techniques and mechanisms for collapse will be apparent to those of skill in the art, and are within the scope of the present disclosure.

Additionally, FIGS. 30A-30B illustrate the disc implant device 332 with the plurality of radial arms 344 in an alternating pattern, from one segment 344' to the next. In such embodiments, each set of radial arms is off-set from the adjacent set or segment 344' of radial arms. For example, where a first segment 344' of radial arms is configured in a first orientation, a second set of radial arms can be oriented in a second, different orientation, off-set from the first orientation, as shown. For example, such an offset may depend on how many arms are in a segment, and may be half the angle between adjacent arms of a given set. For example, such offset may be at an angle from 1 degree to 60 degrees, or from 15 degrees to 45 degrees, or from 25 degrees to 35 degrees, or at an angle of approximately 30 degrees (e.g., where there are 6 arms, each 60 degrees apart).

FIGS. 31A-31E illustrate another embodiment of an implant device 432, similar to implant 332, but with somewhat different features. For example, implant device 432 similarly includes arm segments 344', each arm 344 being formed from a rising arm member 344a and a falling arm member 344b, connected by a compliant hinge mechanism 343. While the implant 432 includes 6 arm members 344 per segment 344', it is shown as including 8 joint ridges 342 in each joint segment 342', rather than simply having 6 joint ridges per segment 342'. The $1^{st}$ and $5^{th}$ joint ridges 342 are "blank", in that they are not connected to any arm member 342, so that when this implant device 432 is folded or rolled to assume its generally cylindrical configuration, it has an octagonal cross section in the joint segment 342', but only 6 of the 8 sides of the octagonal cross sectional shape are attached to arm members 344. FIGS. 31E-31F illustrates what such a configuration looks like, once radially expanded and axially collapsed.

Implant device 432 is also shown as including one or more tension wires 354 associated with each arm segment 344'. Tension wire 354 is shown as running through the compliant hinge mechanism 343, connecting adjacent compliant hinge mechanisms 343 associated with each arm member 344, to one another, effectively joining the arms to one another, at the compliant hinge mechanisms, as well as at the joint ridges of joint segment 342'. The wires 354 are shown as connecting 3 such arms together (e.g., half of the arms within a given segment 344'). The ends of the wires are shown as wrapping around the first and third such arms, so as to be aligned with the 1$^{st}$ and 5$^{th}$ "blind" joint ridge structures 342. Such blind ridge joint structures 342 (the 1$^{st}$ and 5$^{th}$ locations of such) are also shown as including a key 342a and a corresponding keyhole 342b in the opposite side blind ridge joint (e.g., a tongue and groove arrangement), to provide for mating between such key and keyhole structures when the implant is folded or rolled into the generally cylindrical configuration. An adhesive, solder, braze, weld or similar material could be used to secure the key in the keyhole structure, so that once folded or rolled, the configuration 332B (generally cylindrical) cannot revert to configuration 332A (generally planar). Such key and keyhole structures can thus be used to secure such a generally cylindrical configuration, and provide overall stability under load. For example, under a vertical compressive load, the arms will have a tendency to flare out, while the tongue and groove feature helps to keep the arms in place. FIG. 31C illustrates how the tension wires 354 become positioned, once the implant is axially collapsed and radially expanded, where the tension wires help to maintain the radially extended arms in their desired spacing and orientation, with one wire 354 being oriented towards a top of the disc space, and the other wire 354 being oppositely oriented, towards a bottom of the disc space. While "top" and "bottom" are referenced, it will be appreciated that the implant could be rotated, so that the wires (and arrangement of 3 radial arms) could be oriented towards the sides of the disc space, rather than the top and bottom, as particular positioning of the implant in the disc space may vary, depending on need. For example, such an arrangement of 3 sets of radial arm members being oriented towards the top and another 3 sets of radial arm members being oriented towards the bottom can provide 50% surface area engagement and 50% surface area exposure of the implant with the interior surface of the cleaned disc.

Where a tension wire 354 is provided, such wire 354 may be formed from the same material as the remainder of device 432 (e.g., titanium, stainless steel, PEEK, another suitable implantable polymer, a titanium alloy, such as Ti-6A1-4V). In an embodiment, the tension wire 354 may be formed from braided wire (e.g., Ti-6A1-4V braided wire).

While compliant hinge mechanisms 343 are shown as including a pyramidal structure 356 as described previously, for providing angled faces that engage with correspondingly angled faces of the rising and falling arms 344a, 344b, such pyramidal structure 356 is optional, and may be excluded from the compliant hinge mechanism 343 that connects rising arm 344a to falling arm 344b.

It should be appreciated that while the Figures illustrate a disc implant device 332 wherein each set of radial arms comprises 6 radial arms, the disc implant device described herein may comprise more or less than 6 radial arms. In an embodiment, each set may include at least 3 arms, at least 4 arms, at least 5 arms, or at least 6 arms (e.g., from 3 to 12, from 4 to 10, or from 6 to 8).

Returning to FIGS. 24-25, these Figures show the implant in place. During advancement, the disc implant device 332 is in the generally cylindrical folded configuration 332B (e.g., see FIGS. 28A-28B), and once a given segment of arms of the disc implant device 332 is inside the cleared disc space, that segment of arms of the implant can be axially collapsed and radially expanded, filling the disc space, and allowing additional axial room for entrance of the adjacent arm segment. This process can be repeated, until the disc space has been substantially filled by a series of radially expanded, axially collapsed arm segments, each section separated by a joint segment. This is beneficial because the generally cylindrical folded, rolled configuration 332B of the disc implant device 332 has a smaller diameter and lower profile than the radially expanded configuration, and thus will need a smaller incision and corresponding path through which to travel through the patient's body until it is introduced inside the cleared disc space. By way of example, the implant can be advanced into position, housed within a tube or sleeve, the sleeve or tube holding the implant in the generally cylindrical configuration, and as one segment leaves the sleeve or tube, such segment may be biased so as to radially deploy on its own, without any further actuation needed.

Such a procedure and implant device allows a relatively rigid and supportive implant structure to be inserted through the curved posterior to lateral pathway provided, advantageously providing supportive structure within the disc space. Such may be used in combination with, or alternative to introduction of any biologic grafting material introduced into the cleared disc space. For example, once such an implant has been deployed, an appropriate biologic graft material may be employed, to facilitate the long-term success of the fusion. Finally, the guidewire 322 and cannula 320 can be removed, and the incision closed.

Unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, less than 1%, less than 0.1%, or less than 0.01% of the stated amount, value, or condition. As used herein, the term "between" includes any referenced endpoints. For example, "between 2 and 10" includes both 2 and 10.

Ranges between any values disclosed herein are contemplated and within the scope of the present disclosure (e.g., a range defined between any two values (including end points of a disclosed range) given as exemplary for any given parameter).

As used in this specification and the appended claims, the singular forms "a," "an" and "the" include plural referents unless the context clearly dictates otherwise.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A disc implant device comprising:
a body comprising a series of generally cylindrical arm segments, each generally cylindrical arm segment being separated from an adjacent arm segment by a joint segment, each arm segment including a plurality of arm members comprising a plurality of rising arm members and a plurality of falling arm members; wherein the body comprises alternating arm segments separated by joint segments;
wherein the arm segments include a compliant hinge mechanism structure between each respective rising arm member and falling arm member, so that each arm segment is configured to form a plurality of radially extending arms when a given arm segment of the disc implant device is axially collapsed and radially expanded along the compliant hinge mechanism structure, such that the plurality of radial arms form one or more sets of radially extending arms, adjacent segments of radially extending arms being separated by a joint segment therebetween, and
wherein the joint segments between arm segments comprise a tongue and groove or other key and keyhole structures that mate with one another when the arm segment between respective joint segments is radially expanded and axially collapsed.

2. The disc implant device of claim 1, wherein each joint segment comprises a plurality of joint ridges connected to one another by a compliant mechanism structure between adjacent joint ridges, the compliant mechanism structure associated with the joint ridges providing the implant with flexibility along its longitudinal length.

3. The disc implant device of claim 1, wherein the radially extending arms of a given arm segment are spaced apart from one another at an angle from 1 degree to 60 degrees, or from 15 degrees to 45 degrees, or from 25 degrees to 35 degrees, at an angle of approximately 45 degrees, or at an angle of approximately 30 degrees.

4. The disc implant device of claim 3, wherein the radially extending arms of a given arm segment are equally spaced apart from one another.

5. The disc implant device of claim 4, wherein radially extending arms of a given arm segment are spaced apart from one another at an angle of approximately 45 degrees, wherein there are 6 arms, with 3 arms of each segment oriented towards a top, and 3 arms of each segment oriented towards a bottom, wherein the radially extending arms are configured to provide 50% surface area contact between the implant device and an interior surface of a cleaned disc.

6. The disc implant device of claim 1, wherein the plurality of radially extending arms comprises one or more sets of radially extending arms, wherein each set of radially extending arms included in the plurality of radially extending arms includes at least three radial arms.

7. The disc implant device of claim 1, wherein the plurality of radially extending arms comprises one or more sets of radially extending arms, wherein each set of radially extending arms included in the plurality of radially extending arms includes from 3 to 12 radially extending arms.

8. The disc implant device of claim 1, wherein the disc implant device is flexible so as to be capable of assuming a curved configuration, when in a generally cylindrical configuration, resembling a series of sausage links.

9. The disc implant device of claim 8, wherein the disc implant device can assume either a straight or curved configuration when in the generally cylindrical configuration.

10. The disc implant device of claim 8, wherein when the implant device is in the generally cylindrical configuration, the implant has a hexagonal cross section, an octagonal cross-section, or another polygonal cross-section corresponding to a number of radially extending arms included in each arm segment.

11. The disc implant device of claim 1, further comprising:
a hollow generally cylindrical hole disposed through a center of the disc implant device when in a generally cylindrical configuration, the generally cylindrical configuration resembling a series of sausage links, such that the disc implant device, is slidable along a guide wire passing through such hollow generally cylindrical hole.

12. The disc implant device of claim 1, wherein the body comprises a series of generally cylindrical arm segments and joint segments that is initially in the form of a generally planar rectangular sheet having a first elongated side, a second elongated side opposing the first elongated side, a first end, and a second end opposing the first end, and may be configured into a generally cylindrical configuration for the implant device that resembles a series of sausage links, such configuration being formed by folding or rolling the first elongated side towards the second elongated side.

13. The disc implant device of claim 1, wherein the compliant hinge mechanism between each respective rising arm member and falling arm member of the respective arm member includes a pyramidal structure with angled faces, the angled faces of the pyramidal structure of the compliant hinge mechanism being oriented to face corresponding angled faces of the rising arm and falling arm, so that the angled face of the rising arm engages with an angled face of the pyramidal structure, and the angled face of the falling arm engages with another angled face of the pyramidal structure when the arm member is radially expanded.

14. The disc implant device of claim 1, wherein the compliant hinge mechanism between each respective rising and falling arm members of the respective arm member includes a tension wire that connects adjacent compliant hinge mechanisms together, the tension wire engaging with opposed top and bottom portions of a cleared disc space when implanted in the disc space.

15. The disc implant device of claim 14, wherein the tension wire does not engage with side surfaces of the cleared disc space, between top and bottom surfaces with which it does engage, when implanted in the disc space.

16. The disc implant device of claim 1, wherein the arm members of a given arm segment are in line with corresponding arm members of an adjacent arm segment.

17. A disc implant device comprising:
a body in a form of a generally planar rectangular sheet having a first elongated side, a second elongated side opposing the first elongated side, a first end, and a second end opposing the first end, the body comprising alternating sections of joint segments alternated with arm segments, each arm segment including a plurality of rising arm members and falling arm members with a compliant hinge mechanism structure disposed therebetween;
wherein upon folding of the first side towards the second side, the generally planar rectangular sheet assumes a generally cylindrical configuration resembling a series of sausage links, defined by alternating segments of joint segments and arm segments, each of the arm segments being axially collapsible and radially expandable by pressing the first end of the body towards the second end of the body, wherein the joint segments between arm segments comprise a tongue and groove or other key and keyhole structures that mate with one another when the arm segment between such joint segments is radially expanded and axially collapsed.

\* \* \* \* \*